United States Patent [19]
Wechter et al.

[11] Patent Number: 6,150,402
[45] Date of Patent: Nov. 21, 2000

[54] NATRIURETIC COMPOUNDS

[75] Inventors: William J. Wechter; David E. Murray; Darko Kantoci, all of Redlands; Barry H. Levine, Oakland; Elaine J. Benaksas, Yorba Linda, all of Calif.

[73] Assignee: Loma Linda University Medical Center, Loma Linda, Calif.

[21] Appl. No.: 08/290,430

[22] Filed: Aug. 15, 1994

[51] Int. Cl.$^7$ .................................................. A61K 31/355
[52] U.S. Cl. .......................................... 514/458; 549/408
[58] Field of Search ............................. 549/408; 514/458

[56] References Cited

U.S. PATENT DOCUMENTS

| | | | |
|---|---|---|---|
| 3,726,904 | 4/1973 | Habicht et al. | 549/468 |
| 3,947,473 | 3/1976 | Scott et al. | 260/345.5 |
| 4,237,130 | 12/1980 | Cragoe et al. | 514/444 |
| 4,321,270 | 3/1982 | Sundeen | 514/320 |

FOREIGN PATENT DOCUMENTS

| | | |
|---|---|---|
| 0 003 484 | 12/1978 | European Pat. Off. . |
| 0 036 160 | 9/1981 | European Pat. Off. . |
| 0 173 899 A2 | 3/1986 | European Pat. Off. . |
| 0 205 872 A1 | 12/1988 | European Pat. Off. . |
| 0 326 987 A2 | 8/1989 | European Pat. Off. . |
| 0 369 082 | 5/1990 | European Pat. Off. . |
| 0 413 668 A2 | 2/1991 | European Pat. Off. . |
| 0 441 116 | 8/1991 | European Pat. Off. . |
| 0 512 899 | 11/1992 | European Pat. Off. . |
| 1120763 | 7/1968 | France . |
| 27 54 068 A1 | 6/1978 | Germany . |
| 41 21 468 A1 | 1/1993 | Germany . |
| 412 933 | 11/1966 | Switzerland . |
| 421 072 | 3/1967 | Switzerland . |
| 1 590 939 | 6/1981 | United Kingdom . |

OTHER PUBLICATIONS

Noal Cohen, Rocco Lopresti, Gabriel Saucy; A Novel Total Synthesis of (2R, 4'R, 8'R)–α–Tocopherol (Vitamin E). Construction of Chiral Chromans from an Optically Active, Nonaromatic Precursor; *Journal of the American Chemical Society*, 101:22, Oct. 24, 1979, pp 6710–6716.

U. Gloor, J. Würsch, U. Schwieter, O. Wiss; Resorption, Retention, Verteilung und Stoffwechsel des D,L–α–Tocopheramins, d,I–N–Methyl–γ–Tocopheramins und des γ–Tocopherols im Vergleich zum d,l–α–Tocopherol bei der Ratte; *Helvetica Chimica Acta*, vol. 49, 1966, No. 266–267, pp 2303–2312.

CA, p. 615, vol. 98, 1983; 98:71933r and JP, A, 57 145 871 (EISAI) Sep. 9, 1982; Hydroxychromanpropionic acid derivatives.

*Chemical Abstracts*, p. 416, vol. 100, 1984; 100: 136378v and J. Lipid Res., vol 25, No. 1, 1984, Engl., pp 40–48; Novel urinary metabolite of d–δ–tocopherol in rats.

*Chemical Abstracts*, p. 490, vol. 81, 1974; 151742s and Chem. Pharm. Bull., vol. 22., No. 3, 1974, JP pp 566–575; Ubuquinone and related compounds.

*Chemical Abstracts*, vol. 72, 1970, pp 383–384; 78856q and JP, A,6 927 026 (Taisho Pharmaceutical.) Nov. 11, 1969; Tocopheronolactone.

*Chemical Abstracts*, p. 2845, vol. 68, 1968; 29435k and JP, A, 1 303 467 (Yamanouchi) Jul. 28, 1967; Novel toluquinone derivatives.

*Chemical Abstracts*, p. 2512, vol. 69, 1968; 27057k and JP, A, 6 723 024 (Yamanouchi) Nov. 9, 1967; Novel 3,4–dimethoxytoluquinones.

CA: 106: 84395 (1985).

CA 120: 266482 (1993).

Derwent Abstract of JP 63208557 (A).

Free Radical Biology & Medicine, vol. 16 No. 4; Reduction of Myocardial Infarct Size in Rat by IRFI–048, A Selective Analogue of Vitamin E.

Pharmacology 1994; 48 pp. 157–166; Protective Effects of IRFI–016, a New Antioxidant Agent, in Myocardial Damage, following Coronary Artery Occlusion and Reperfusion in the Rat.

Research Communications in Chemical Pathology and Pharmacology, vol. 76, No. 3, pp. 287–303, Jun. 1992; IRFI–016, A New Radical Scavenger, Limits Ischemic Damage Following Coronary Artery Occlusion in Rats.

*Primary Examiner*—Amelia Owens
*Attorney, Agent, or Firm*—Knobbe, Martens, Olson & Bear, LLP.

[57] ABSTRACT

Compounds, methods and compositions are provided for inducing natriuresis in a mammal. Methods for isolating and synthesizing the natriuretic compounds are also provided. Therapeutic methods using the natriuretic compounds are also provided. The natriuretic compounds are capable of inducing sodium excretion in a mammal without inducing corresponding prolonged potassium excretion.

11 Claims, 5 Drawing Sheets

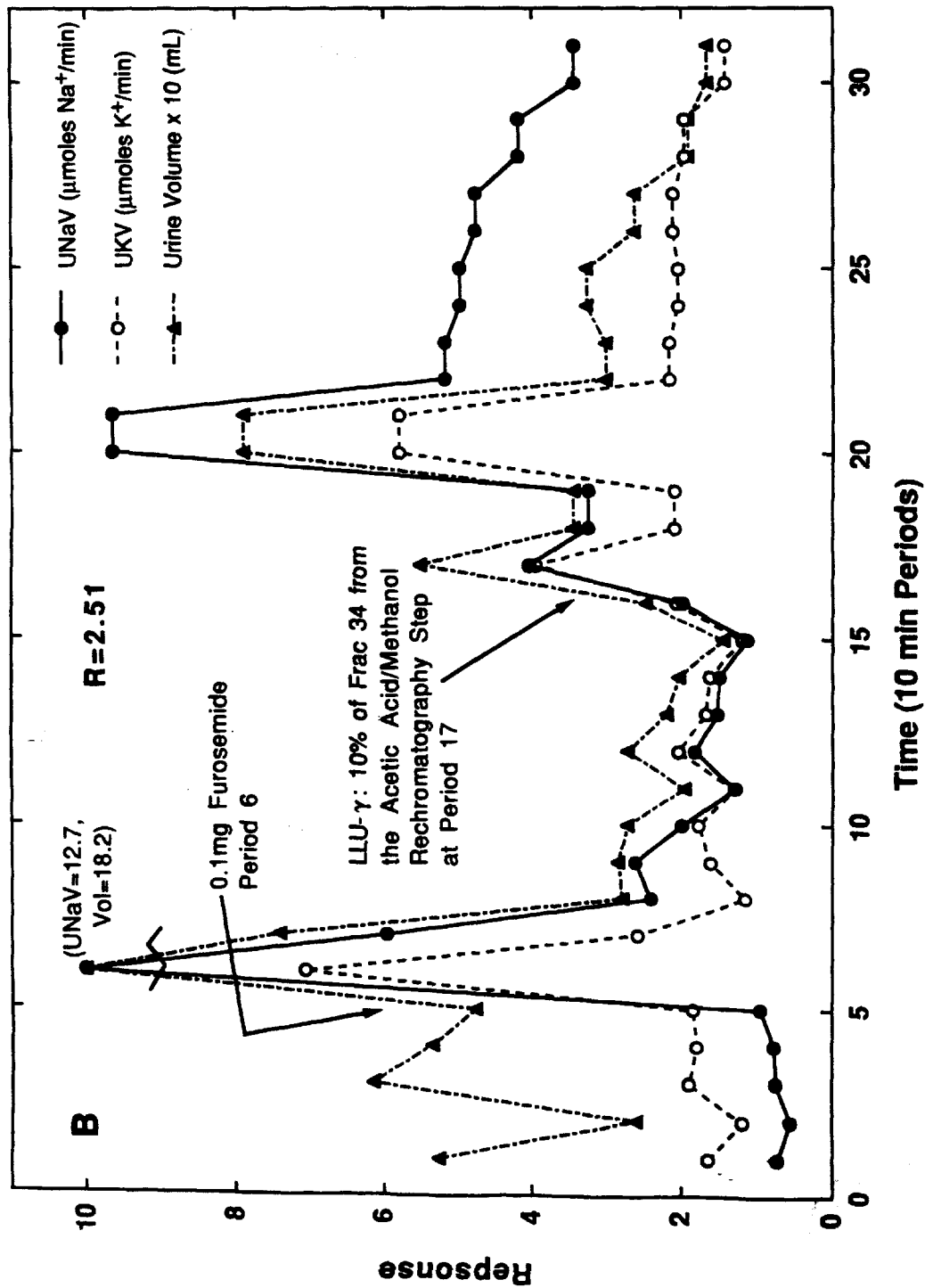

NATRIURETIC COMPOUNDS

BACKGROUND OF THE INVENTION

1. Field of the Invention

This invention relates to compounds which can be used to increase sodium excretion in man or other mammals. The invention also relates to methods for purifying the compounds, and to pharmaceutical compositions and therapeutic methods utilizing the compounds.

2. History of Related Art

The adverse effects of high sodium concentration are considered to be at least partially responsible for a number of diseases, including hypertension, congestive heart failure, cirrhosis of the liver and renal disease leading to chronic renal failure. Understanding the nature of the system controlling sodium excretion, therefore, may lead to an effective therapy or cure for these diseases.

Over thirty years ago, de Wardener formulated that a "natriuretic hormone" must exist for sodium excretion regulation. In his classic parabiotic experiments in the dog, it was observed that prolonged increased sodium excretion (hereinafter referred to as "natriuresis") was produced in a normal animal by the infusion of plasma from a volume expanded animal. See de Wardener et al., *Clin. Sci.* 21, 249–258 (1961). Since then, considerable effort has been employed by researchers in the field to isolate and identify the factors involved in the regulation of sodium excretion.

Most investigators in this field believe that this putative humoral substance may be responsible not only for sustained natriuresis, but also for inhibition of sodium transport and increased vascular reactivity. The latter two effects occur via inhibition of the $Na^+/K^+$-ATPase, also known as the sodium pump. Therefore, many in vitro assays have been used to search for the hormone based on the tenet of sodium pump inhibition by the hormone. These assays include $Na^+/K^+$-ATPase inhibition, ouabain displacement from the pump, and cross-reaction of isolates from various in vivo sources with anti-cardiac glycoside antibodies. (See Wechter, et al., *Prog. Drug Res.* 34, 231–260 (1990). Research has focused on isolation of natriuretic factors acting on the $Na^+/K^+$-ATPase pump. Numerous putative natriuretic compounds (sometimes identified as hormones) have been found using the above-mentioned methodologies. See, e.g., Wechter et al., *Prog. Drug Res.* 34 231–260 (1990). For example, Bricker et al., U.S. Pat. No. 5,106,630 identified a compound having a steroidal nucleus, a molecular weight of 360 and a molecular formula of $C_{21}H_{28}O_5$ as natriuretic hormone.

Ouabain and digoxin or their isomers having been isolated recently using these methodologies. These materials are not, however, natriuretic. See Ludens et al., *Hypertens.* 17, 923–929 (1991); Mathews et al., *Hypertens.* 17, 930–935 (1991); Tymiak et al., *Proc. Natl. Acad. Sci.* (USA) 90, 8189, 8193 (1993); Goto et al., *Biochem. Biophys. Res. Comm.* 173, 1093–1101 (1990). These and other results indicate that sodium pump inhibitory activity does not necessarily lead to natriuresis. In fact, it is at least as likely to produce kaliuresis. See Sekihara et al., *Life Sci.* 53, 975–980 (1993); Pamnani, et al., *Hypertens.* 18, 316–324 (1991); Smyth et al., *Can. J. Physiol. Pharmacol.* 70, 723–727 (1992); Crabos et al., *Eur. J. Biochem.* 162, 129–135 (1987). Therefore, a natriuretic compound purification process solely using assays based on binding to and/or inhibition of the $Na^+/K^+$-ATPase pump may not lead to the discovery of the putative natriuretic hormone.

In addition, despite decades of efforts, natriuretic compounds had not been isolated in pure form, chemically and structurally defined, or synthesized in the laboratory. Also, as demonstrated above, the above-mentioned methodologies used in the purification process to monitor natriuretic activity fail to measure natriuresis directly. Therefore, prior to the present invention, the putative natriuretic hormone had not been identified.

It would be highly desirable to provide compounds having a natriuretic effect. It would also be desirable to develop a new method to isolate endogenous natriuretic compounds by using an assay measuring natriuresis directly. It would be desirable as well to develop a more effective purification method to obtain substantially pure natriuretic compounds in an amount sufficient for chemical and structural definition.

SUMMARY OF THE INVENTION

In accordance with one aspect of the present invention, there if provided a natriuretic compound having the formula I

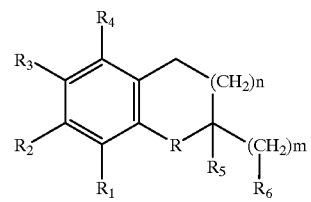

in which

R is O, S, SO, $SO_2$, a secondary or tertiary amine group, a phosphate group, a phosphoester group, or an unsubstituted or substituted methylene group, $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, n is 0 to 3, and m is 0 to 5.

In a more specific embodiment, R is O in formula I. In a preferred embodiment, $R_1$, $R_2$ and $R_5$ are $Ch_3$, $R_3$ is OH, $R_4$ is H, $R_6$ is COOH, n=1 and m=2.

Also provided is a natriuretic compound having the formula II

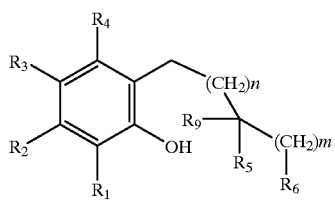

wherein
- $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring,
- $R_3$ and $R_4$ independently are H, Oh, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring,
- $R_5$ is H, OH, alkyl, aryl, alkenyl, alkynyl, aromatic, ester or unsubstituted or substituted amine,
- $R_6$ is COOH, $COOR_7$, $CONH_2$, $CONHR_7$, $CONR_7R_8$, $NH_2$, $NHR_7$, $NR_7R_8$, or a carboxylate salt,
- $R_7$ and $R_8$ independently are unsubstituted or substituted alkyl, aryl, alkaryl, aralkyl, alkenyl or alkynyl,
- $R_9$ is hydroxyl or unsubstituted or substituted alkoxyl,
- n is 0 to 3, and
- m is 0 to 5.

There is additionally provided a natriuretic compound having the formula III

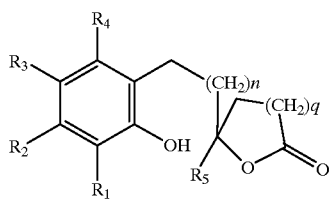

wherein
- $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring,
- $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring,
- $R_5$ is H, OH, alkyl, aryl, alkenyl, alkynyl, aromatic, ester or unsubstituted or substituted amine,
- n is 0 to 3, and
- q is 0 to 4.

There is further provided a natriuretic compound having the formula IV

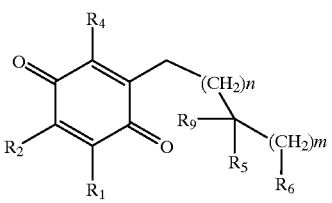

wherein
- $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring,
- $R_4$ is H, OH, alkyl, aryl, alkenyl, alkynyl, aromatic, ether, ester, unsubstituted or substituted amine, amide, halogen or unsubstituted or substituted sulfonyl,
- $R_5$ is H, OH, alkyl, aryl, alkenyl, alkynyl, aromatic, ester or unsubstituted or substituted amine,
- $R_6$ is COOH, $COOR_7$, $CONH_2$, $CONHR_7$, $CONR_7R_8$, $NH_2$, $NHR_7$, $NR_7R_8$, or a carboxylate salt,
- $R_7$ and $R_8$ independently are unsubstituted or substituted alkyl, aryl, alkaryl, aralkyl, alkenyl or alkynyl,
- $R_9$ is hydroxyl or unsubstituted or substituted alkoxyl,
- n is 0 to 3, and
- m is 0 to 5.

There is also provided a natriuretic compound having the formula V

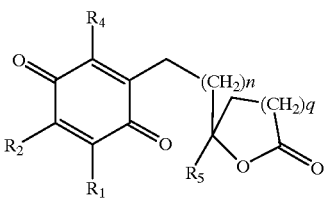

wherein
- $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring,
- $R_4$ is H, OH, alkyl, aryl, alkenyl, alkynyl, aromatic, ether, ester, unsubstituted or substituted amine, amide, halogen or unsubstituted or substituted sulfonyl,
- $R_5$ is H, OH, alkyl, aryl, alkenyl, alkynyl, aromatic, ester or unsubstituted or substituted amine,
- n is 0 to 3, and
- q is 0 to 4, with the proviso that said compound is not 4-methyl-6-(5,6-dimethylbenzochinoyl)-4-hexanolid.

In another aspect, the present invention provides a compound having the formula Ia

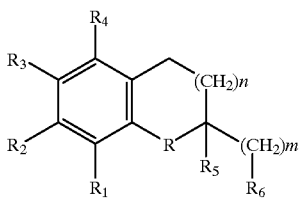

Ia in which
R is O, S, SO, SO$_2$, a secondary or tertiary amine group, a phosphate group, a phosphoester group, or an unsubstituted or substituted methylene group, R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, heterocyclic ring, R$_3$ and R$_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, R$_5$ is H, OH, alkyl, aryl, alkenyl, alkynyl, aromatic, ester or unsubstituted or substituted amine, R$_6$ is COOH, COOR$_7$, CONH$_2$, CONHR$_7$, CONR$_7$R$_8$, NH$_2$, NHR$_7$, NR$_7$R$_8$, or a carboxylate salt, R$_7$ and R$_8$ independently are unsubstituted or substituted alkyl, aryl, alkaryl, aralkyl, alkenyl or alkynyl, n is 0 to 3, and m is 0 to 5.

Compounds within the foregoing formula can be employed per se or in pharmaceutical compositions for stimulating sodium excretion and for treatment of conditions including hypertension or other edematous conditions, ischemia, angina pectoris and HIV infection or AIDS. In preferred embodiments of the foregoing compounds, (i) when R is O, R$_1$, R$_2$ and R$_5$ are CH$_3$, R$_3$ and R$_6$ are OH, and R$_4$ is H, m=2 to 5;

(ii) when R is O R$_1$ is H or CH$_3$, R$_2$ is H, CH$_3$, C(CH$_3$)$_3$ or CH(CH$_3$)$_2$, R$_3$ is OH or CH$_3$COO, R$_4$ is CH$_3$ or CH(CH$_3$)$_2$, R$_5$ is H, CH$_3$ or CH$_2$CH$_3$, and R$_6$ is H, OH, OCH$_3$, OCH$_2$CH$_3$ or NH$_2$, m=1 to 5;

(iii) when R is O, R$_1$ and R$_5$ are Ch$_3$, R$_2$ and R$_4$ are H, R$_3$ is OH or CH$_3$COO, and R$_6$ is OH or CH$_3$O, m is not 2;

(iv) when R is O, R$_1$, R$_2$ and R$_5$ are CH$_3$, R$_3$ is OH or CH$_3$COO, R$_4$ is alkyl having at least two carbon atoms, and R$_6$ is H, OH or ester, m=1; and (v) when R$_1$, R$_2$ and R$_5$ are methyl, R$_3$ and R$_6$ are OH and R$_4$ is alkyl, m=2.

Yet another aspect of the present invention provides a method of obtaining, from a mammalian sample, a substantially purified natriuretic compound capable of increasing sodium excretion in the urine of a mammal. In the inventive method, at least a portion of the sample is subjected to gel filtration using a solution of ammonium acetate as an eluant, with retention only of material appearing immediately after a salt peak and having significant absorbance at 280 nm to obtain a post-salt peak material. A biologically active fraction is isolated from the post-salt peak material by repeated reverse-phase high pressure chromatography using an eluate selected from the group consisting of pyridinium acetate/methanol, acetic acid/methanol and isocratic acetic acid/methanol. The biologically active fraction is then subjected to silica gel high pressure chromatography to obtain a chromatography product. The chromatography product having biological activity is recovered using isopropanol/hexane as eluant. Finally, the compound is separated from the biologically active fraction by removing solvent from the fraction.

In a preferred embodiment, the purification method further comprises the steps of extracting from the post-salt peak material an isopropanol/diethyl ether soluble compound and isolating a biologically active fraction from the extract by repeating the reverse-phase high pressure chromatography step.

In another aspect of the present invention, an in vivo bioassay is employed to directly measure the natriuretic increases of the active fractions.

A further aspect of the invention provides methods for producing natriuretic compounds as described above. One preferred method includes the step of reacting a compound of the formula VI

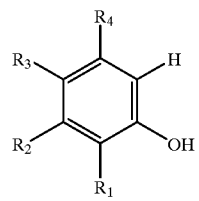

VI in which

R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, and R$_3$ and R$_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, with a vinyl lactone of the formula VII

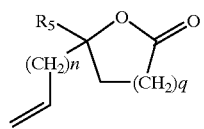

VII in which

R$_5$ is H, alkyl, aryl, alkenyl, alkynyl, aromatic or ester, n is 0 to 3, and q is 0 to 4.

Compounds of formula I above, with R=O and R$_6$=COOH, can be produced according to the foregoing method. Compounds of formulae II–V can be produced by oxidation and/or dehydration of the corresponding formula I compound, for example by reaction with a solution of ferric chloride (FeCl$_3$).

As a byproduct of the foregoing synthetic method, compounds of formula VIII are produced:

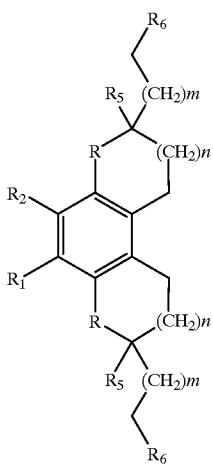

VIII

These compounds are also useful as natriuretic compounds according to the instant invention.

Another aspect of the present invention provides a pharmaceutical composition useful for stimulating sodium excretion in the urine of a mammal which comprises a pharmaceutically acceptable carrier and a compound as described above in an amount effective to stimulate sodium excretion. The compositions can also comprise a mixture of two or more of the compounds of the invention, with the total amount of the compounds being effective to stimulate sodium excretion.

Still another aspect of the present invention provides a method of treating a mammal suffering from hypertension, ishcemia (in particular cardiac ischemia), angina pectoris or an edematous condition which comprises the step of orally or parenterally administering a pharmaceutical composition of the present invention to the mammal.

Yet another aspect of the present invention provides a method of treating a mammal suffering from HIV infection or AIDS which comprises the step of orally or parenterally administering a pharmaceutical composition of the present invention to the mammal.

The invention is defined in its fullest scope in the appended claims and is described below in its preferred embodiments.

BRIEF DESCRIPTION OF THE DRAWINGS

FIGS. 3A–B provide the results of the in vivo bioassay of LLU-α (A) and LLU-γ (B). Natriuesis (UNaV; closed circles), Kaliuresis (UKV; open circles), and diuresis (Urine volume; closed triangles) were measured.

DETAILED DESCRIPTION OF THE PREFERRED EMBODIMENTS

Figure 1:
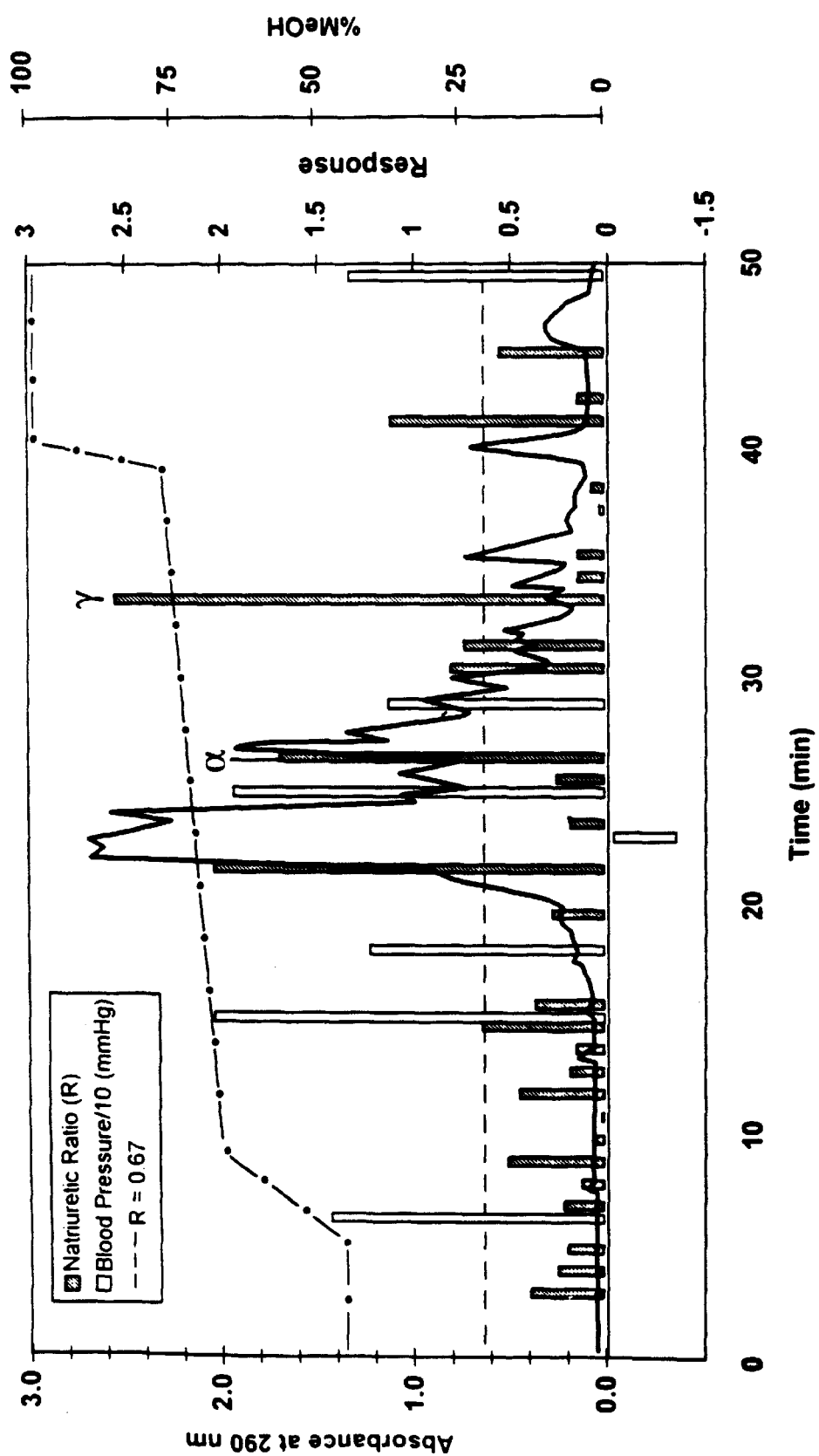
FIG. 1 provides the HPLC chromatogram, elution profile at 290 nm (solid line), of an aqueous acetic acid/methanol rechromatography step according to the inventive method and the natriuretic and blood pressure responses of the corresponding fractions.
Figure 2:
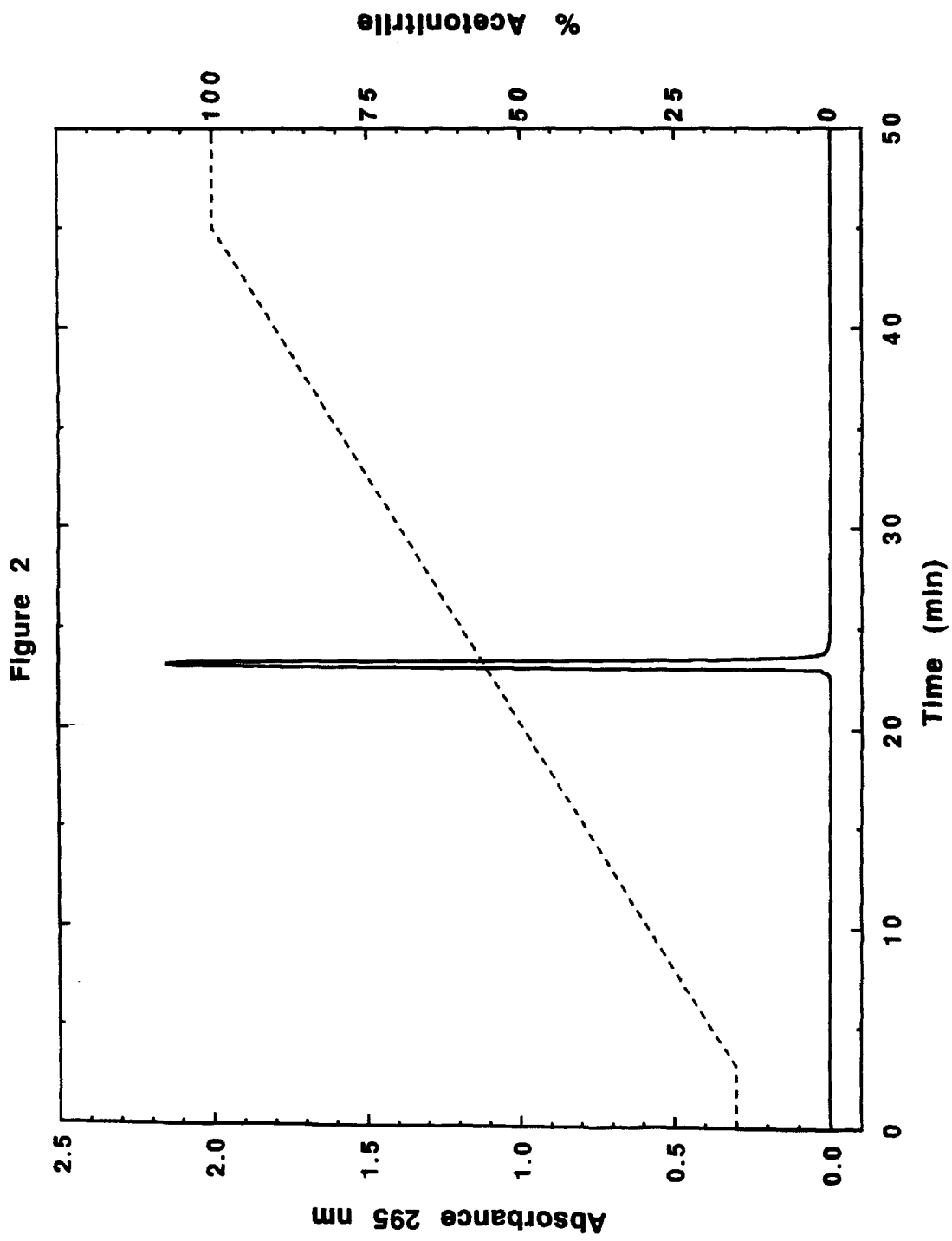
FIG. 2 provides a chromatogram, elution profile at 295 nm (solid line), of an aliquot of a purified natriuretic compound, namely LLU-α, on the acetic acid/acetonitrile RP-HPLC system. LLU-α, purified through the seventh purification step of the extraction procedure, was subjected to analytical HPLC using acetic acid/acetonitrile in an additional RP-HPLC step.

In accordance with the present invention, novel natriuretic compounds are provided for the stimulation of sodium excretion in mammals and for the treatment of high sodium concentration related diseases in humans.

As used herein, the term "natriuretic compound" refers to a compound which increases the rate of sodium excretion in a mammal upon administering the compound to the mammal. The term "natriuretic compound" also refers to both the native compound and in vitro or in vivo modifications which retain natriuretic activity. It is understood that limited modifications, substitution or deletions of functional groups may be made without destroying the biological activity. Moreover, it will be recognized by those skilled in the arts of chemistry and pharmaceutical preparation that many derivatives can be made which are biologically and chemically equivalent to, or even more active than, the indicated compounds hereinafter.

Examples of equivalent compounds include esters, ethers, amides and salts of the foregoing compounds.

Furthermore compounds of the present invention can be mixed with, bonded to or conjugated with compounds having the same or a complementary range of biologic activities to obtain the benefits of the present invention.

"Substantially purified," when used to describe the state of the natriuretic compound, denotes the compounds essentially free of proteins, steroids, and other material normally associated or occurring with natriuretic compounds in its native environment.

As used herein, the term "post salt peak" refers to material eluted from a G-25 Sephadex column which appears immediately after the sodium, potassium, urea and creatinine containing fractions which has uv. absorbance at 280 nm.

A material is "biologically active" if it is capable of increasing natriuresis in an in vivo assay as described herein.

One aspect of the invention provides a novel natriuretic compound having the formula I

I

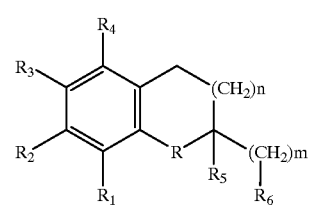

in which

R is O, S, SO, $SO_2$, a secondary or tertiary amine group, a phosphate group, a phosphoester group, or an unsubstituted or substituted methylene group, $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, n is 0 to 3, and m is 0 to 5.

As used herein, the term "substituted" denotes the presence of one or more substituent such as alkyl, aryl, alkaryl, aralkyl, ether or halogen. More particular substituents include $C_{1-6}$ unbranched or branched alkyl, such as methyl, ethyl, propyl, n-butyl, sec-butyl and tert-butyl, and $C_{6-12}$ aryl, particularly phenyl.

In a preferred embodiment, R is O. Also preferably, n=1. Preferably, m=2.

$R_6$ preferably is COOH.

Preferably, $R_3$ is H or OH. Also preferably, $R_4$ is H or $CH_3$.

In a preferred embodiment, $R_1$, $R_2$ and $R_5$ are $CH_3$.

Exemplary preferred compounds of formula I include those in which R is O, $R_1$, $R_2$ and $R_5$ are $CH_3$, $R_3$ is OH, $R_4$ is H or $CH_3$, $R_6$ is COOH, n=1 and m=2.

Other exemplary preferred compounds of formula I includes those in which R is O, $R_1$, $R_2$ and $R_5$ are $CH_3$, $R_3$ is H, $R_4$ is H or $CH_3$, $R_6$ is COOH, n=1 and m=2.

In a preferred embodiment, $R_7$ is a $C_{1-6}$ alkyl group, in particular $CH_3$.

In another preferred embodiment, $R_3$ is OH.

Compounds within the scope of the present invention can also be obtained by modifying the above recited formula in numerous ways while preserving natriuretic activity. Examples of such active derivatives include compounds of formulae II–V, below.

In all formulae described herein, moieties having like designations are considered to correspond to each other as like moieties in related compounds.

Natriuretic compounds within the scope of the instant invention also include compounds having the formula II

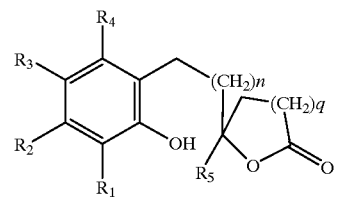

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, $R_9$ is hydroxyl or unsubstituted or substituted alkoxyl, n is 0 to 3, and m is 0 to 5.

In a preferred embodiment, $R_1$, $R_2$ and $R_5$ are $CH_3$. Preferably, $R_3$ is OH $R_4$ preferably is H.

Additionally, it is preferred that n=1. Preferably M=2.

In a preferred embodiment, $R_6$ is $COOCH_2CH_3$ and $R_9$ is OH. In another preferred embodiment, $R_6$ is COOH and $R_9$ is $CH_3CH_2O$.

Specific examples include the following:

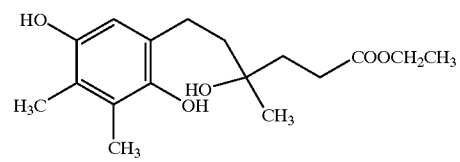

Natriuretic compounds of the invention also include compounds having the formula III

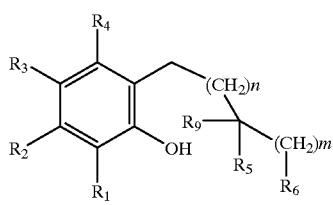

wherein $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, n is 0 to 3, and q is 0 to 4.

In preferred embodiments, n=1. Also preferred are compounds in which m=2.

Exemplary natriuretic compounds of formula III include the following:

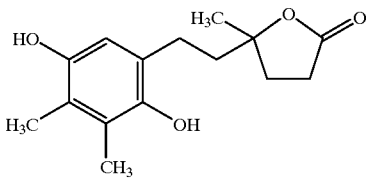

The instant invention also includes natriuretic compounds having the formula IV

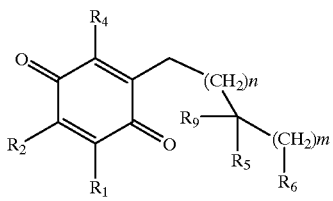

wherein
$R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_4$ is H, OH, alkyl, aryl, alkenyl, alkynyl, aromatic, ether, ester, unsubstituted or substituted amine, amide, halogen or unsubstituted or substituted sulfonyl, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, $R_9$ is hydroxyl or unsubstituted or substituted alkoxyl, n is 0 to 3, and m is 0 to 5.

Preferably n=1. Also, preferably m=2.

Specific compounds of the invention according to formula IV include:

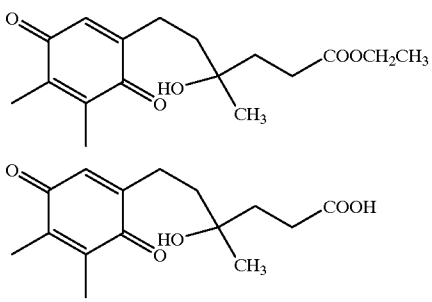

Natriuretic compounds of formula V are also included in the instant invention:

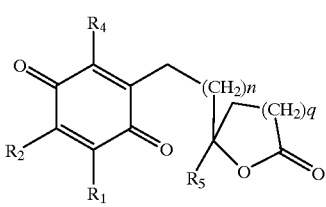

wherein
$R_1$ and $R_2$ independently are H, Oh, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_4$ is H, OH, alkyl, aryl, alkenyl, alkynyl, aromatic, ether, ester, unsubstituted or substituted amine, amide, halogen or unsubstituted or substituted sulfonyl, $R_5$ is H, OH, alkyl, aryl, alkenyl, alkynyl, aromatic, ester or unsubstituted or substituted amine, n is 0 to 3, and q is 0 to 4.

Preferred embodiments are those in which n=1. Also, it is preferred that m=2.

Included in the inventive compounds of formula V are:

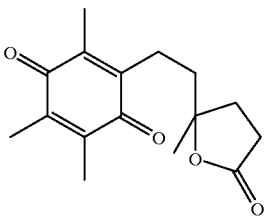

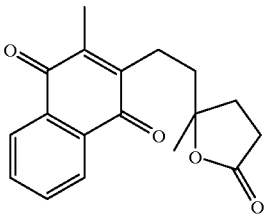

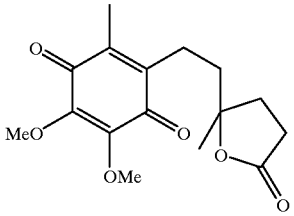

In accordance with another aspect of present invention, compounds are provided having the formula Ia

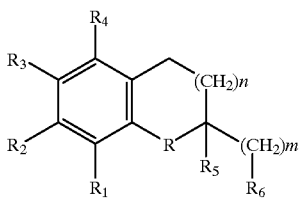

in which

- R is O, SO, $SO_2$, a secondary or tertiary amine group, a phosphate group, a phosphoester group, or an unsubstituted or substituted methylene group,
- $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring,
- $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring,
- $R_5$ is H, OH, alkyl, aryl, alkenyl, alkynyl, aromatic, ester or unsubstituted or substituted amine,
- $R_6$ is COOH, $COOR_7$, $CONH_2$, $CONHR_7$, $CONR_7R_8$, $NH_2$, $NHR_7$, $NR_7R_8$, or a carboxylate salt,
- $R_7$ and $R_8$ independently are unsubstituted or substituted alkyl, aryl, alkaryl, aralkyl, alkenyl or alkynyl,
- n is 0 to 3, and
- m is 0 to 5.

In preferred embodiments, (i) when R is O, $R_1$, $R_2$ and $R_5$ are $CH_3$, $R_3$ and $R_6$ are OH, and $R_4$ is H, m=2 to 5;

(ii) when R is O $R_1$ is H or $CH_3$, $R_2$ is H, $CH_3$, $C(CH_3)_3$ or $CH(CH_3)_2$, $R_3$ is OH or $CH_3COO$, $R_4$ is $CH_3$ or $CH(CH_3)_2$, $R_5$ is H, $CH_3$ or $CH_2CH_3$, and $R_6$ is H, OH, $OCH_3$, $OCH_2CH_3$ or $NH_2$, M=1 to 5;

(iii) when R is O, $R_1$ and $R_5$ are $Ch_3$, $R_2$ and $R_4$ are H, $R_3$ is OH or $CH_3COO$, and $R_6$ is OH or $CH_3O$, m is not 2;

(iv) when R is O, $R_1$, $R_2$ and $R_5$ are $CH_3$, $R_3$ is OH or $CH_3COO$, $R_4$ is alkyl having at least two carbon atoms, and $R_6$ is H, OH or ester, m=1; and (v) when $R_1$, $R_2$ and $R_5$ are methyl, $R_3$ and $R_6$ are OH and $R_4$ is alkyl, m=2.

Certain natriuretic compounds of the present invention have been isolated in substantially pure form. The natriuretic compounds can be obtained from a variety of sources, including urine, hypothalamus, adrenal, plasma, blood and cultured cells. Human uremic urine is the preferred source, although normal human urine may also be used.

Compounds of the present invention are shown to have natriuretic and diuretic activity in mammals. One of the isolated natriuretic compounds according to present invention, which is named as LLU-α, has a molecular weight of 264.1362 and a molecular formula of $C_{15}H_{20}O_4$. The compound has the following properties: a major ultraviolet absorbance peak at about 210 nm; a broad secondary peck at about 295 nm; instability in dilute base; capability of esterification by reaction with $CH_2N_2$. The compound is capable of increasing sodium excretion in the urine in mammals without a corresponding increase in potassium excretion, and does not cause a significant change in mean arterial pressure. The compound additionally acts as a cardio-selective free radical scavenger. LLU-α (systematic name: 6-hydroxy-2,7,8-trimethylchroman-2-propanoic acid) has the following structure:

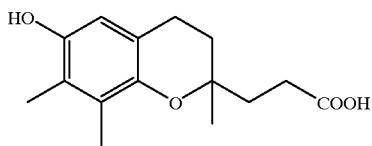

In accordance with formula I, R is O, $R_1$, $R_2$ and $R_5$ are $CH_3$, $R_3$ is OH, $R_4$ is H, $R_6$ is COOH, n=1 and m=2 for LLU-α.

The instant invention also provides another isolated natriuretic compound, named LLU-γ, which has the following properties: a major ultraviolet absorbance peak at about 220 nm; a secondary peak at about 268 nm; high instability in the presence of $O_2$ or in dilute base. It is capable of increasing sodium excretion in mammalian urine without a corresponding increase in potassium excretion, although potassium excretion (kaliuresis) may be observed occasionally after infusion of the compound into conscious rats. In addition, it does not cause a significant change in mean arterial pressure and it shows no inhibition of the sodium pump.

The biological activity of the natriuretic compounds can be determined by a number of assay techniques which include, but are not limited to the in vivo bioassay described herein to measure the natriuresis and the mean arterial pressure (MAP) in conscious rats after infusion of the compounds of present invention into conscious rats. The natriuretic compounds of present invention are shown to have natriuretic and diuretic activity in the in vivo bioassay. For example, in the in vivo bioassay, natriuresis can be observed when a natriuretic compound of the present invention is infused to the conscious rat. However, the MAP measured by connecting the arterial catheter of the conscious rat to a blood pressure transducer has no significant changes upon adding the natriuretic compounds of the present invention. Generally, the natriuretic compounds show no inhibition in the $Na^+/k^+$-ATPase inhibition assay.

Natriuretic compounds and compositions of the present invention can find use in numerous therapeutic applications, such as, e.g., inducing natriuresis and diuresis. Thus, compounds of formulae I–V and VIII, or compounds produced from a compound of formula Ia in which R=O (hereinafter a compound of formula Ib) by oxidation or dehydration, can find use as therapeutic agents in the treatment of various edematous states such as, for example, congestive heart failure, cirrhosis of the liver accompanied by edema or ascites, renal diseases such as nephrotic syndrome, in addition to hypertension, and renal failure due to ineffective renal perfusion or reduced glomerular filtration rate.

In addition to natriuretic properties, it has been unexpectedly discovered that compounds within the scope of formulae I–V and VIII can be useful in treating ischemia and angina pectoris. The present invention thus includes compounds and compositions useful in treating these conditions. It has also been unexpectedly discovered that compounds within the scope of formulae I–III and VIII can also relieve oxidative stress, and thus inhibit apoptosis and subsequent loss of immune cells. Oxidative stress and resulting apoptosis have been implicated in HIV infection (see, e.g., Greenspan et al. *Immunology Today*, vol. 15, No. 5, pp. 209–213 (1994)). Thus, the present invention also provides compounds and compositions which can be useful in treating patients suffering from HIV infection or AIDS.

Compounds and compositions within the scope of the present invention can be administered to mammals for veterinary use such as with domestic animals, and clinical use in humans in any conventional manner. For example, a composition can be prepared which includes one or more of the present compounds together with a pharmaceutically acceptable carrier.

The amount of the inventive natriuretic compound, or compounds, administered is therapeutically effective if it can increase sodium excretion. A typical initial dose would be from 0.1 μg to 1 mg/kg, more preferably 4 μg to 50 μg/kg of the host body weight. Later doses can be adjusted in accordance with the clinical effects of the initial dose. The total daily dose can consist of a single individual dose or multiple doses given at intervals. Dosages within these ranges can also be administered by constant infusion over an extended period of time, usually exceeding 24 hours, until the desired therapeutic benefits have been obtained.

Amounts of the compounds described herein which are therapeutically effective against hypertension, ischemia, etc., can also be determined through routine investigation.

The compounds can be administered neat, as mixtures with other physiologically acceptable active or inactive materials such as moistening agents, flavoring agents, binding agents, and extenders, as well as other compounds having pharmacological activities, such as other diuretics which increase the distal delivery of sodium or other antihypertensive agents. It may also be administered with physiologically suitable carriers such as, for example, water or normal saline. The compounds can be administered orally, nasally or parenterally, for example, by injection. Injection can be subcutaneous, intravenous, or by intramuscular injection. It may also be administered as pharmacologically acceptable salts.

The pharmaceutical compositions can take the form of tablets, capsules, injectable solutions and suspensions, oral solutions, and other formulations intended for pharmaceutical use. For example, a composition intended for use in a tablet could contain active material, calcium stearate, calcium sulfate, microcrystalline cellulose, peppermint oil, polysorbate 80, povidone, and pregelatinized starch.

Natriuretic compounds of the invention can be purified by a number of methods, particularly those exemplified herein. In a preferred method within the invention, collected urine is processed by ultrafiltration (≦3 kDa), gel filtration chromatography (G-25) and extraction with isopropanol and diethyl ether. The organic soluble material is then subjected to sequential high-performance liquid chromatography, while assaying for the natriuretic, $Na^+/K^+$-ATPase pump inhibition and vascular relaxant activity of the fractions. In an alternative embodiment, the material from gel filtration chromatography may be directly subjected to sequential high-performance liquid chromatography without the organic solvent extraction.

In a further alternative embodiment, the inventive compounds can be synthesized using methods known to those skilled in the art. One such method is the method described by J. Weichet et al., Czech. Chem. Commun. 24, 1689–1694 (1959), the disclosure of which is hereby incorporated by reference. This method can readily be adapted by one of ordinary skill in the art to provide a method of synthesizing the compounds of the present invention.

A preferred synthetic method includes the step of reacting a compound of the formula VI

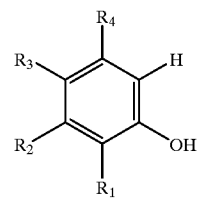

in which $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, and $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, with a vinyl lactone of the formula VII

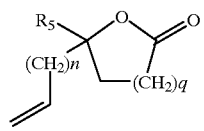

in which $R_5$ is H, alkyl, aryl, alkenyl, alkynyl, aromatic or ester, n is 0 to 3, and q is 0 to 4.

In a preferred embodiment of the foregoing synthesis, $R_3$ is OH. Preferably, $R_4$ is not simultaneously OH. A preferred compound of formula VI is a hydroquinone, for example 2,3-dimethyl-1,4-hydroquinone.

A preferred vinyl lactone of formula VII is γ-methyl-γ-vinylbutyrolactone ($R_5$=$CH_3$, n=1, Q=1).

In carrying out the foregoing reaction, preferably a catalyst is used, such as metallic or non-metallic salt. Specific types of catalyst include non-metallic salts which form complexes with a solvent, particularly a catalyst such as boron trifluoride diethyl etherate.

In carrying out the foregoing reaction, preferably an aprotic or protic solvent is employed, in particular an aprotic such as dioxane. The catalyst and/or the vinyl lactone is preferably diluted in the selected solvent.

Preferably the synthesis is carried out at an elevated temperature, such as 100–110° C.

In a preferred embodiment, the foregoing reaction mixture is diluted with an aprotic or protic solvent, particularly an aprotic solvent such as dietheyl ether.

The desired product preferably is obtained from concentrated supernatant which is purified, for example, using an RP-HPLC column or silica gel. Preferred eluents for RP-HPLC include mixtures of water, acetonitrile and acetic acid. Preferred solvents for silica gel include ethyl acetate and hexane. Other purification methods, such as crystallization, can be used. Also, other eluents, such as hexane and dimethyl ketone, can be employed.

The foregoing synthesis produces a racemic mixture, of which typically one enantiomer is active while the second enantiomer is less active or inactive. The racemate can be employed in compositions according to the invention, with adjustment of the quantity to account for the presence of the inactive enantiomer. Alternatively, the racemate can be resolved using conventional methods, and the active enantiomer identified and utilized. All anantiomeric forms of the compounds described herein are specifically contemplated as being within the scope of the instant invention.

As a byproduct of the foregoing synthesis, derivative compounds of formula VIII are produced:

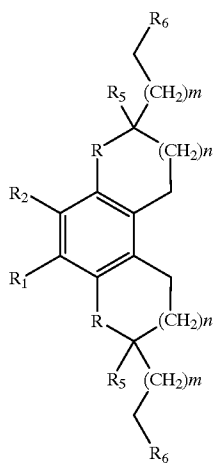

VIII

These compounds can also be employed as natriuretic compounds according to the instant invention. Exemplary compounds of formula VIII include the following benzodipyran derivatives:

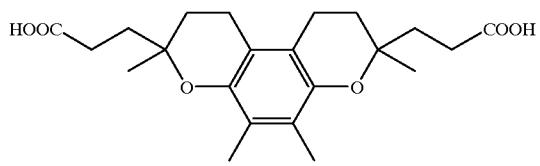

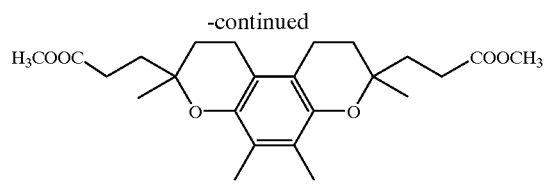

All stereoisomeric forms of the foregoing compounds, including meso compounds and diastereomeric pairs, are specifically contemplated as being within the scope of the instant invention.

Di-oxidized and/or di-hydrated derivatives of the compounds of formula VIII can be obtained in a manner analogous to those used to obtain compounds of formulae II–V from the compounds of formula I.

As mentioned previously, natriuretic compounds of the instant invention can be modified by formation of esters, amides, etc. Esterification can be carried out, for example, by reaction with a solution of a diazoalkane, or with an an anhydride or an acyl chloride. Amides can be formed by reaction with ammonia or an amine.

Natriuretic compounds of formulae II–V can be derived from the corresponding natriuretic compounds produced by the foregoing method, for example, by oxidation. In a preferred embodiment of this process, when $R_4=H$, $R_5$ is not $CH_3$.

A preferred oxidizer for the foregoing method is a solution of ferric chloride. Other oxidants, such as $KMnO_4$, $SeO_2$, $CrO_3$, $H_2O_2$, m-chloroperbenzoic acid, Caro acid, $OsO_4$, potassium ferricyanide, silver chromate or sodium perborate, can also be used.

Scheme 1 illustrates the relationship between exemplary compounds of formulae I–V. Note that Scheme 1 depicts the relationships between the S-enantiomers. The same relationships exist between the corresponding R-enantiomers. A wide variety of natriuretic compounds within the scope of the instant invention can be obtained in the manner illustrated.

SCHEME 1

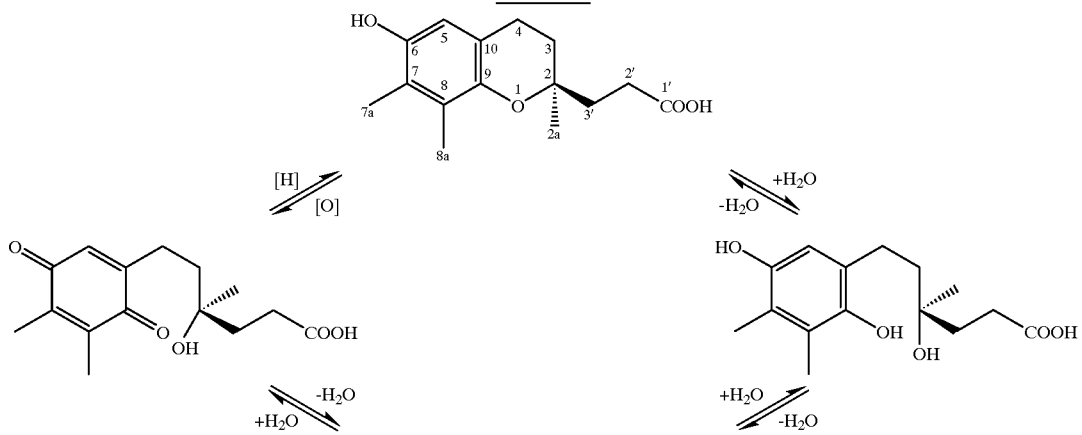

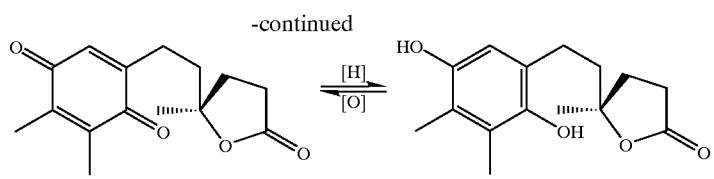

The following examples are intended to illustrate, but not limit the invention. While they are typical of those that might be used, other procedures known to those skilled in the art may be alternatively employed. In the examples, the following abbreviations are used:

| | |
|---|---|
| EI | electron impact |
| FR | furosemide response |
| FT-IR | Fourier-transform infrared spectroscopy |
| HPLC | high performance liquid chromatography |
| MAP | mean arterial pressure |
| MDBK | Madin-Darby bovine kidney |
| MS | mass spectrometry |
| NMR | nuclear magnetic resonance |
| PBS | phosphate buffered saline |
| $R_n$ | natriuretic ratio |
| RP-HPLC | reverse-phase high performance liquid chromatography |
| SR | sample response |
| UNaV | urine concentration of sodium X urine volume per time |

EXAMPLE 1

Isolation of Natriuretic compound

Human uremic urine was initially processed by ultrafiltration (3 kDa) and lyophilization, followed by isolation of the post-salt fraction from Sephadex G-25 gel filtration chromatography, following the procedure of Benaksas et al., *Life Sci.* 52, 1045–1054 (1993), the entire disclosure of which is herein incorporated by reference. See Table I (first purification step).

The crude material was further purified by one of two procedures. One procedure involved four sequential HPLC steps, and the second procedure included organic solvent extraction followed by up to five sequential HPLC steps. Table I summarizes the two methods.

TABLE I

Summary of steps used in the chromatographic and extraction isolation procedures

| Purification Step | Chromatographic Method | Extraction Method |
|---|---|---|
| First | 3K ultrafiltration, lyophilization and G-25 | 3K ultrafiltration, lyophilization and G-25 |
| Second | 0.2 M pyridinium acetate pH 5.5/Methanol $C_{18}$ RP-HPLC | Sequential extraction with isopropanol/diethyl ether yielding soluble compounds |
| Third | 1st 0.2 M acetic acid/methanol $C_{18}$ RP-HPLC | 1st 0.2 M acetic acid/methanol $C_{18}$ RP-HPLC |
| Fourth | 2nd (modified) 0.2 M acetic acid/methanol $C_{18}$ RP-HPLC | 2nd (modified) 0.2 M acetic acid/methanol $C_{18}$ RP-HPLC[b] |
| Fifth | Isopropanol/hexane[a] | Isocratic 0.2 M acetic acid/methanol[c] |
| Sixth | | Isopropanol/hexane silica gel HPLC |
| Seventh | | 50 mM acetic acid/acetonitrile $C_{18}$RP-HPLC[d] |

[a]Amount of resulting material of LLU-γ was so small that further purification was not pursued.
[b]LLU-γ was further purified by a chromatography step not used in the main purification scheme.
[c]This HPLC step was only used for isolation of LLU-α.
[d]LLU-α methyl ester was also purified using these HPLC conditions.

1. Chromatographic Isolation Method

A four-step sequential HPLC procedure was employed which was a modification of the procedure reported by Benaksas et al., noted above. The first $C_{18}$RP-HPLC (Table I, step 2) was performed on a Beckman Ultraphere ODS column (10 μm; 21.2×150 mm) eluting at 6 mL/minute with a gradient of 0.2 M pyridinium acetate, pH 5.5 (A) and methanol (B) (80% A:20% B for 22 minutes, a linear gradient to 40% A:60% B over 48 minutes, a linear gradient to 100% B over 10 minutes). The column was washed with 70% toluene:30% methanol, then re-equilibrated at initial conditions for at least 20 minutes. This column wash method was implemented in every chromatography employing a methanol eluant. The eluant was monitored with a Beckman 166 UV detector at 290 nm. Eighty (80) one-minute fractions were collected and dried under reduced pressure in a centrifugal vacuum concentrator.

Based on bioassay evaluation (see Example 2, below) and chromatographic comparison of previous HPLC runs, fractions 50–80 were combined for the second RP-HPLC step (Table I, third step). A Beckman Ultrasphere ODS ($C_{18}$) column (5 μm; 10×250 mm) was eluted at 2 mL/minute with a gradient of 0.2 M acetic acid (A), methanol (B) and 70% toluene: 30% methanol (C), (60% A:40% B for 5 minutes, a linear gradient to 50% A:50% B over 5 minutes, a linear gradient to 30% A:70% B over 55 minutes, a linear gradient to 100% B over 2 minutes, 100% B for 3 minutes, 100% C for 8 minutes, 100% B for 7 minutes). The eluant was monitored for fluorescence (exc. 310–410 nm; emm. 475–610 nm: Beckman 157 detector) and absorbance at 290 nm with a Beckman 168 diode array detector. Ultraviolet spectra were collected by diode array at 2 second intervals over the range of 202–390 nm. Eighty (80) one-minute fractions were collected.

As discussed in detail in Example 2, two natriuretically active isolates (LLU-α and LLU-γ) in particular were identified. The region encompassing the two natriuretically active isolates was pooled and rechromatographed using a modified acetic acid/methanol gradient for the third RP-HPLC (Table I, fourth step). The solvents and column were the same as the second RP-HPLC above; however, the gradient was changed (60% A:40% B for 5 minutes, a linear gradient to 40% A:60% B over 5 minutes, a linear gradient to 30% A:70% B over 28 minutes, a linear gradient to 100% B over 2 minutes, 100% B for 3 minutes, 100% C for 8 minutes) and only fifty (50) one-minute fractions were collected.

During the first aqueous acetic acid-methanol RP-HPLC step (Table I, third step), chromophore markers corresponding to natriuretically active materials could be identified when processing different batches of urine. By rechromatographing fractions 38–68 and 63–66 using a modified acetic acid-methanol method (Table I, fourth step) employing a shorter gradient, the two natriuretically active marker chromophores, designated LLU-α and LLU-γ, reproducibly eluted at 27.8 and 35.4 minutes, respectively (FIG. 1). This fourth purification step allowed consistent identification of natriuretically active crude isolates.

The LLU-α natriuretic isolate was subjected individually to normal phase chromatography on silica gel (Beckman Ultrasphere, 5 μm, 10×250 mm) eluting at 2 mL/minute with a hexane (B) isopropanol (A) gradient (6% A:94% B for 25 minutes, a linear gradient to 100% A over 30 minutes, 100% A for 20 minutes, a linear gradient to 6% A:94% B over 5 minutes and an equilibration period at 6% A:94% B for 35 minutes). Seventy (70) one-minute fraction were collected from this fifth purification step (Table I). Fluorescence was monitored as described above. The wavelength monitored for each of the isolates was selected based upon its absorbance spectrum from the prior chromatogram. Chromatography of the first isolate (LLU-α) was monitored at 295 nm and that of the second (LLU-γ) at 267 nm. Fractions exhibiting UV absorbance characteristic of LLU-α and LLU-γ were bioassayed (see below).

2. Extraction Method

Freeze-dried material obtained from the gel filtration chromatography was stirred with 9 volumes of isopropanol for 18 hours. The isopropanol solution was then removed and evaporated to dryness on a rotary evaporator under reduced pressure. The resulting thick, dark brown oil from the isopropanol soluble phase was weighed and then alternately stirred and sonicated for 6 hours and finally stirred for an additional 18 hours, with 10 volumes of diethyl ether. The ether solution was then decanted and 4 volumes of ether were added to the remaining insoluble material. After stirring for 72 hours, the ether solution was again decanted. Two volumes of deionized distilled water and 2 volumes of diethyl ether were added to the residue. After stirring for 2 hours, the ether phase was separated and the aqueous phase was washed three times with one volume of ether. The combined ether extracts were washed with saturated aqueous NaCl and water, and taken to dryness on a rotary evaporator under reduced pressure. The residue was redissolved in 95% ethanol and again taken to dryness.

The ether extraction residue was dissolved in 40% aqueous methanol and subjected to acetic acid-methanol RP-HPLC (Table I, third step). The chromatographic region from LLU-α to LLU-γ, as identified by their characteristic UV spectra, was pooled, dried, re-suspended and chromatographed on the second modified acetic acid-methanol RP-HPLC (Table I, fourth step). Only LLU-α and LLU-γ were detected after this chromatography step.

Isocratic acetic acid-methanol RP-HPLC (Table I, fifth step) was then performed on LLU-α. Employing a Beckman Ultrasphere ODS ($C_{18}$) column (5 μm; 10×250 mm), LLU-α was eluted at 2 mL/minute with 45% 0.2 M acetic acid and 55% methanol for 35 minutes collecting seventy (70) half-minute fractions. The eluant was monitored for absorbance at 290 nm (diode array) and fluorescence. LLU-α was identified by its UV spectrum and subjected to silica gel HPLC (Table I, sixth step).

The fractions containing LLU-α from the silica gel HPLC were pooled and subjected to another $C_{18}$ RP-HPLC step. In this seventh purification step (Table I), a Beckman Ultrasphere ODS column (5 μm; 4.6×250 mm) was eluted at 1 mL/minute with a gradient of 50 mM acetic acid (A) and 45 mM acetic acid in acetonitrile (B) (85% A:15% B for 3 minutes, a linear gradient to 100% B over 42 minutes, 100% B for 5 minutes). The column was washed with 1:1 methylene chloride: acetonitrile for 5 minutes followed by re-equilibration at initial conditions for 16 minutes. Chromatography was monitored at 265 and 295 nm with the diode array detector. Fifth (50) half-minute fractions were collected staring at 10 minutes.

The extraction purification procedure increased the yield of isolated LLU-α by about 50%. In the chromatographic procedure, encompassing a total of five purification steps, less than 1 mg of LLU-α was obtained from about 105 g of lyophilized G-25 material (yield less than $9 \times 10^{-4}$%). Approximately 1.8 mg of LLU-α results from the extraction procedure (seven purification steps) applied to about 155 g of lyophilized G-25 product (yield approximately $1.2 \times 10^{-3}$%). The two additional RP-HPLC steps of this procedure led to essentially pure LLU-α. Likewise, the yield of LLU-γ appeared to increased comparably.

Figure 4:
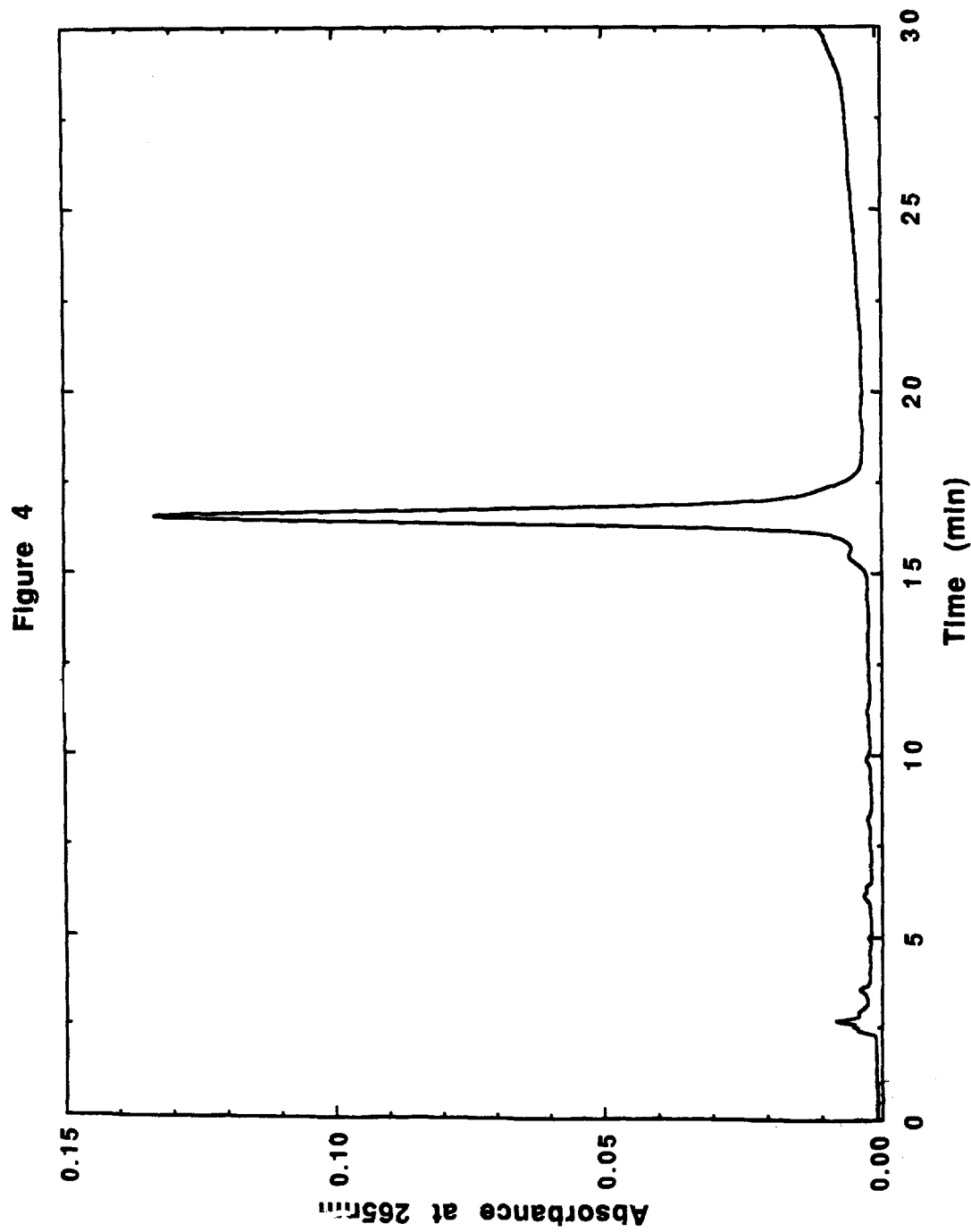
FIG. 4 provides a chromatogram, elution profile at 265 nm (solid line), of the final step of purification of a natriuretic compound, namely LLU-γ, on the trifluoroacetic acid/acetonitrile RP-HPLC system. LLU-γ, purified through the fourth purification step of the extraction procedure, was subjected to a final purification step using trifluoroacetic acid/acetonitrile in an additional RP-HPLC step.

LLU-γ from the modified acetic acid-methanol RP-HPLC chromatography step (Table I, fourth step) can be further purified using a method compatible for LC-MS. In this purification step, a Beckman Ultrasphere ODS column (5 μm, 4.6×250 mm) was eluted isocractically at 1 mL/minute with 0.1% trifluoroacetic acid, 40% acetonitrile, and 60% water for 30 minutes. LLU-γ from the previous chromatographic step elutes at 16.5 minutes. Between runs the column is washed with 0.1% trifluoroacetic acid in acetonitrile for 10 minutes, followed by re-equilibration at initial conditions for 10 minutes. Chromatography was monitored at 265 and 230 nm with a diode array detector. LLU-γ was collected as a single fraction. Results are shown in FIG. 4.

TABLE II

Chemical characteristics of the natriuretic LLUs

|  | LLU-α | LLU-γ |
| --- | --- | --- |
| Exact Mass | 264.1373 | ND[a] |
| Empirical Formula | $C_{15}H_{20}O_4$ | ND |
| UV Characteristics | λmax 205 nm<br>λmax 294 nm | λmax 220 nm<br>λmax 268 nm |
| Functional Groups Determined by IR | carboxyl<br>hydroxyl<br>aryl ether | ND |
| Physical Properties | Unstable in dilute Base<br>Unstable in $CDCl_3$ | Unstable when Purified<br>Very Unstable in Dilute Base |
| Reaction with $CH_2N_2$ | HNF-α methyl ester $C_{14}H_{19}O_2CO_2CH_3$ MW 278.1515 + Other Products | ND |

[a]ND: Not Determined

Isolated from early fractions of silica gel HPLC of LLU-α was the drug naproxen, which was being administered to some urine donors. Its identity was determined by NMR and verified by comparison with the NMR spectrum of commercial naproxen. Naproxen serves as an additional marker during the silica gel HPLC.

3. Treatment of LLU-α with $CH_2N_2$

Diazomethane was generated by treatment of 1-methyl-3-nitro-1-nitrosoguanidine (112 mg, 760 μmol) with 400 μL 50% KOH (aq). The diazomethane was distilled into 1 mL diethyl ether at −7° C. This solution was then added to 700μg (2.6 μmol) LLU-α in 0.5 mL diethyl ether at 0° C. The reaction mixture was warmed to ambient temperature, then allowed to stand for 40 minutes. Solvent was removed under a stream of $N_2$ and the residue dissolved in 15% 45 mM acetic acid in acetonitrile/85% 50 mM acetic acid and subjected to the acetic acid—acetonitrile RP-HPLC purification step as described above (seventh step). The approximate yield of the ester was 53%. Methyl esterification of LLU-α followed by RP-HPLC yielded essentially pure LLU-α methyl ester. The methyl ester was synthesized to further the characterization of LLU-α. LLU-α methyl ester eluted as an apparently homogenous single peak from acetic acid—acetonitrile RP-HPLC. A total of approximately 0.9 mg of LLU-α methyl ester was isolated and subjected to chemical characterization by ultraviolet, infrared, $^{13}C$- and $^1H$- NMR and mass spectroscopy. The physical chemical characteristics, molecular weight and inferred molecular formula of both LLU-α and its methyl ester are listed in Table II.

EXAMPLE 2

Bioassays for Biological Activity

1. In vivo bioassay

The assay for natriuresis in conscious rats has been described previously (see Benaksas et al., above). The assay is briefly reiterated here. Female Sprague-Dawley (Harlan) rats (200–250 g) were cannulated in the femoral artery and vein for monitoring of mean arterial pressure (MAP) and infusion of saline and samples, respectively. The bladder was catheterized for collection of urine in ten-minute periods. Furosemide (0.4 mg/kg bwt; 1 mg/mL in 0.17% saline) was infused as a positive control at the beginning of the sixth ten-minute period. The sample was infused at the beginning of the seventeenth ten-minute period. Urine was collected for another 150 minutes. The volume of the urine was determined gravimetrically and the $Na^+$ and $K^+$ concentrations determined with a Beckman E2A electrolyte analyzer. From these data the sodium excretion values (UNaV) were calculated.

The natriuretic response of a sample was normalized to the dose of furosemide infused. The net sodium excretion for the infusion of furosemide or sample was calculated as follows. The median sodium excretion value (μmoles $Na^+$/ 10 minute period) for the five periods before infusion of furosemide or sample was used to establish a baseline value for the calculation of ΔUNaV (=μmoles $Na^+$ period−baseline μmoles $Na^+$) for administration of either furosemide or sample respectively. The sum of ΔUNaV for the four periods following infusion of furosemide was the net sodium excreted for furosemide, defined as FR. The sum of ΔUNaV for the fifteen periods following infusion of the sample was the net sodium excreted for the sample defined as SR. The natriuretic ratio $R_n$ (or normalized natriuretic response) of a sample was calculated by dividing SR by FR ($R_n$=SR/FR). A sample is considered natriuretically active if the $R_n$ value for that sample was greater than or equal to 0.67 (greater than 99% confidence limits).

Partially purified LLU-α from silica gel-HPLC (sixth purification step) was assayed for natriuretic activity utilizing the in vivo bioassay. It was active in the 4–8 μg/kg dose range and showed no activity at lower or higher doses (Table III). LLU-α is also active at 8 μg/kg when evaluated in the in vivo bioassay after being further purified on acetic acid/acetonitrile RP-HPLC (seventh step of extraction method).

TABLE III

Dose response of LLU-α present in fractions from the silica gel HPLC step of the extraction procedure from uremic urine

| Fraction | Dose (μg) | Natriuretic Response (R)[a] |
|---|---|---|
| 17 | 0.2 | −0.14 |
|  | 1 | 0.27 |
|  | 2 | 1.14 |
|  | 2 | 0.75 |
|  | 10 | 0.26 |
| 18 | 56.4 | 0.23 |
|  | 224 | 0.02 |
| 19 | 0.2 | 0.24 |
|  | 1 | 0.93 |
|  | 2 | −0.10 |
|  | 2 | 0.82 |
|  | 10 | 0.09 |
| 20 | 2 | 1.32 |
|  | 2 | 0.39 |
| 21 | 2 | −0.06 |
|  | 2 | 0.39 |

[a]Natriuretic ratio greater than 0.67 indicates that a sample is natriuretically active (99% confidence limits).

Figure 3A:
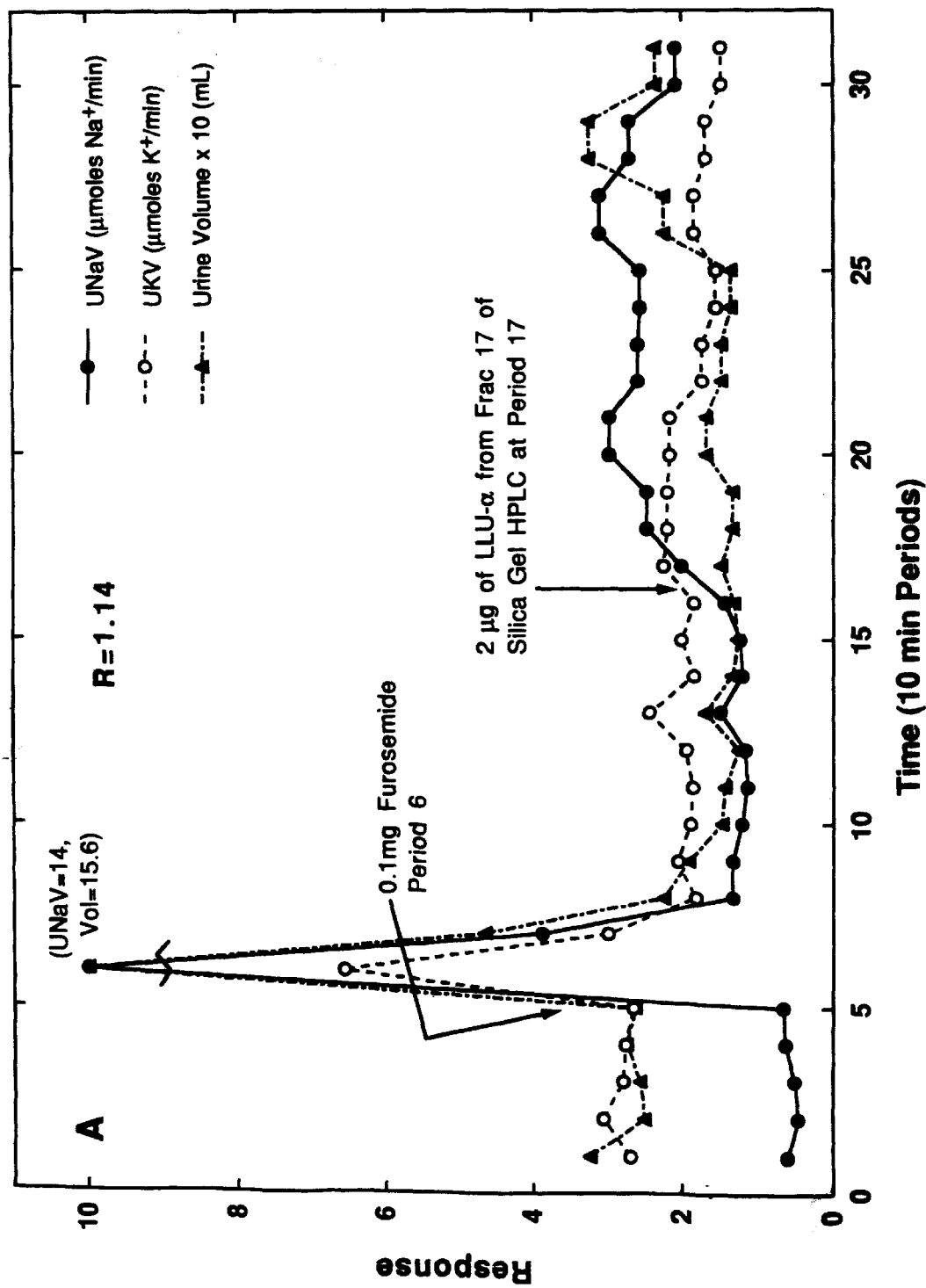

LLU-α and -γ when infused into the rat produced sustained natriuresis (FIGS. 3A and B) with no effect on blood pressure (data not shown). LLU-γ has not been purified sufficiently to obtain a dose-response curve for natriuresis, owing to its instability. LLU-α displays a narrow and biphasic natriuretic dose-response curve (Table III). There was no detectable kaliuresis when LLU-α was infused (FIG. 3A). Some kaliuresis occurred after the infusion of LLU-γ, however, this was not always observed. Neither LLU-α nor -γ caused a significant change in mean arterial pressure.

2. $Na^+/K^+$-ATPase inhibition assay

The assay in MDBK cells has been described previously (see Benaksas et al., above). The assay is described briefly here. Madin-Darby bovine kidney (MDBK) cells (ATCC:CCL22) were maintained in Dulbecco's Modified Eagle's Medium (DMEM) with 5% Fetal Bovine Serum and 5% Bovine Calf Serum in a 5% $CO_2$/95% humidified air atmosphere at 37° C. and split (1:2) once per week.

One day before the assay, cells were plated in a 96-well plate at a density of $5 \times 10^5$ cells/well in DMEM with serum. On the day of the assay the medium was removed and the cells washed with phosphate buffered saline (PBS) before addition of 100 μL of assay media (122 mM NaCl, 1.8 mM $CaCl_2$, 0.8 mM $MgSO_4$, 24 mM $NaHCO_3$, 1 mM sodium pyruvate, 25 mM glucose, 14 mM glycylglycine, 0.2% phenol red, 8 mM $Na_2HPO_4$ 1.15 mM $KH_2PO_4$, pH 8.0) and 100 μl of sample. The plate was preincubated for 30 minutes at 37° C., then chilled on ice for 10 minutes. To each well was added 0.15 μCi $^{86}RbCl$ (Amersham) in 10 μL of assay media. The plate was then incubated at 37° C. for 10 minutes. A portion (100 μL) of the supernatant was counted with 0.5 mL of scintillation cocktail in a liquid scintillation counter. As a control for $Na^+/K^+$-ATPase inhibition, a dose response curve for ouabain in the range of $10^{-5}$–$10^{-8}$ M was obtained. Intra-experiment coefficient of variation for ouabain was 3–15%. Inhibition of $^{86}Rb^+$ uptake by samples was corrected for that uptake which was inhibitable by ouabain.

When LLU-α was assayed in the $Na^+/K^+$-ATPase inhibition assay it exhibited no inhibition in the range of 0.2–200 ng/well. Assay of crude LLU-γ obtained from the acetic acid-methanol RP-HPLC rechromatography step in the sodium pump inhibition assay showed no inhibition of the sodium pump.

EXAMPLE 3

Analytical Spectroscopy

In addition, spectroscopy other than UV was performed. $^{13}$C- and $^1$H-NMR spectra were recorded at 500.1357 MHz in deutero-chloroform (99.9%) in a GN-500 spectrometer (General Electric). High resolution Electron-Impact (EI) mass spectra with a resolution of 2000 were recorded at an ionization voltage of 70 eV, source temperature of 200° C. and introduction of sample by direct probe on a VG7070 EHF high resolution mass spectrometer. Fourier-transform infrared (FT-IR) spectroscopy was performed on a Nicolet 5DX with 4 wavenumber resolution.

The IR and $^{13}$C-NMR spectra of LLU-α provided evidence for the presence of a carboxylic acid group. This explained the tailing of LLU-α observed upon elution from isopropanol/hexane silica gel HPLC (sixth purification step). The presence of a carboxyl group was verified when the reaction of LLU-α with diazomethane resulted in a product that was less polar or RP-HPLC and had an exact mass 14 units greater than LLU-α as determined by MS (Table II). This is consistent with the formation of a methyl ester.

In the following synthesis examples, Examples 4–10 set forth general methods useful to produce a wide range of compounds within the scope of the invention. Examples 11–21 described syntheses of specific compounds.

EXAMPLE 4

Synthesis of Racemic 6-hydroxychromans

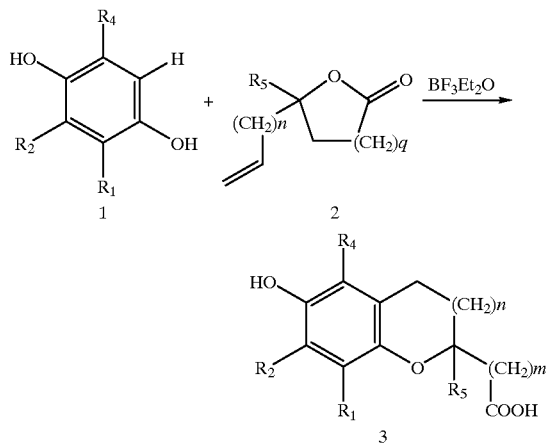

To a solution of hydroquinone 1 (0.01 mol) and a catalyst, preferably boron trifluoride diethyl etherate (0.016 mol) in an organic solvent, preferably dry dioxane (10 mL), is added vinyl lactone 2 (0.016 mol) in an organic solvent, preferably dry dioxane (5.0 mL) over 1–60 minutes, preferably 60 minutes, at 0–150° C., preferably 110° C., under an inert gas. The reaction mixture is stirred for 0 to 8 hours, preferably 0 hours, at the selected temperature, cooled to room temperature, and diluted with an organic solvent, preferably diethyl ether (200 mL). The reaction mixture is then washed with water (100 mL, 2×50 mL), dried over sodium sulfate (Na$_2$SO$_4$), and solvent is removed under reduced pressure to afford a brown oily residue. The residue is dissolved in alcohol, preferably methanol (30 mL), and the alcohol is then removed under reduced pressure. The brown oily liquid or semisolid is further purified by chromatography, preferably on silica gel, to afford pure racemic chroman derivative 3.

EXAMPLE 5

Synthesis of Racemic Chromans

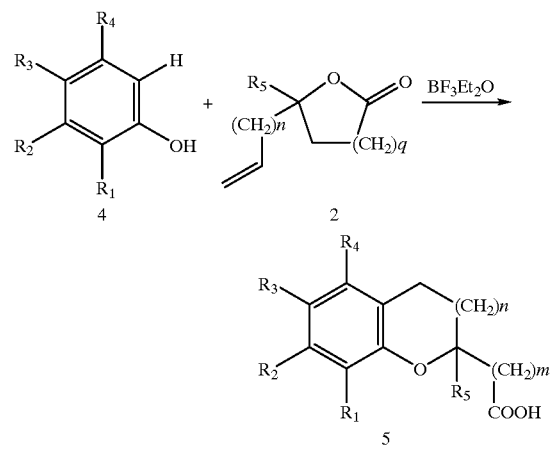

To a solution of phenol 4 (0.01 mol) and a catalyst, preferably boron trifluoride diethyl etherate (0.016 mol) in an organic solvent, preferably dry dioxane (10 mL), is added vinyl lactone 2 (0.016 mol) in an organic solvent, preferably dry dioxane (5.0 mL) over 1–60 minutes, preferably 60 minutes at 0–150° C., preferably 110° C., under an inert gas. The reaction mixture is stirred for 0 to 8 hours, preferably 0 hours, at the selected temperature, cooled to room temperature, and diluted with an organic solvent, preferably diethyl ether (200 mL). The reaction mixture is then washed with water (100 mL, 2×50 mL), dried over sodium sulfate (Na$_2$SO$_4$), and solvent is removed under reduced pressure to afford a brown oily residue. The residue is dissolved in alcohol, preferably methanol (30 mL), and the alcohol is then removed under reduced pressure. The brown oily liquid or semisolid is further purified by chromatography, preferably on silica gel, to afford pure racemic chroman derivative 5.

EXAMPLE 6

Synthesis of Chroman Methyl Esters

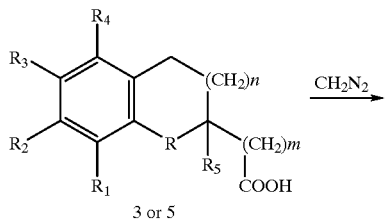

-continued

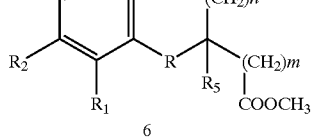

6

Chroman 3 ($R_3$=OH) or 5 (see Examples 4 and 5 above) (0.01 mol) is dissolved in methanol (30 mL), and a solution of diazomethane in ether is added at 0–5° C. until the yellow color of the diazomethane remains. The reaction mixture is left at room temperature for 2–5 hours, solvent is removed, and the desired product 6 is crystallized from a suitable organic solvent.

EXAMPLE 7

Synthesis of Chroman Esters

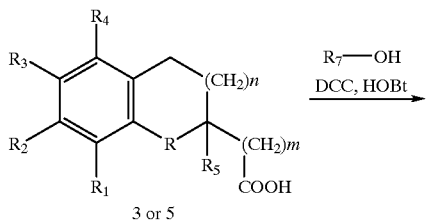

3 or 5

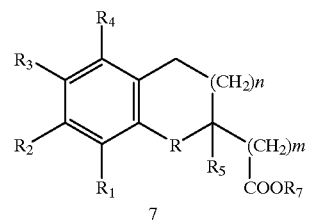

7

Chroman 3 ($R_3$=OH) or 5 (10 mmol) is dissolved in dry tetrahydrofuran (30 mL) with an alcohol $R_7$—OH (12 mmol), 1-hydroxybenzotriazole (10 mmol) and 1,3-dicyclohexylcarbodiimide (11 mmol) at 2–5° C. The reaction mixture is stirred at 2–5° C. for one hour and at 23° C. for one to 20 hours. Precipitated dicyclohexyl urea is filtered, solvent is removed under pressure, and the residue is diluted with ethyl acetate (150 mL). The organic phase is washed with aqueous KHSO$_4$ (10%, 40 mL), water (50 mL) and saturated aqueous hydrogen carbonate (50 mL), and then dried over sodium sulfate. The solvent is removed under reduced pressure, and the residue is purified by chromatography, preferably silica gel, to afford pure racemic ester 7.

EXAMPLE 8

Synthesis of Chroman Amides

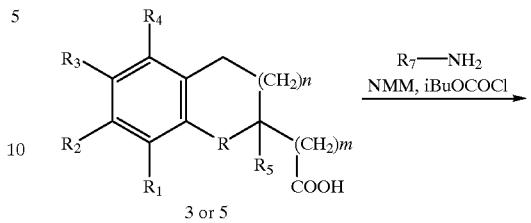

3 or 5

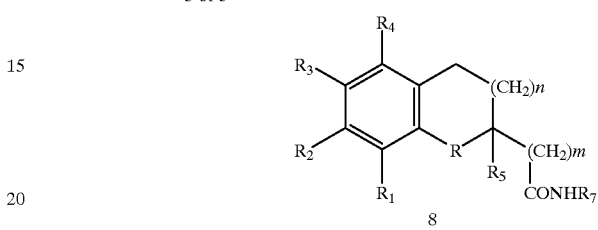

8

Chroman 3 ($R_3$=OH) or 5 (10 mmol) is dissolved in dry tetrahydrofuran (40 mL) and neutralized with N-methylmorpholine. Isobutyl chlorocarbonate (10 mmol) is added, followed one minute later by a selected amine ($R_7$—NH$_2$ or $R_7R_8$—NH), or ammonia (11 mmol). The reaction mixture is allowed to reach room temperature. After stirring at room temperature for 1 hour, THF is removed under reduced pressure, and the residue is taken into ethyl acetate (250 mL). The ethyl acetate solution is successively washed with aqueous KHSO$_4$ (10%, 40 mL), water (50 mL) and saturated aqueous hydrogen carbonate (50 mL), and then dried over sodium sulfate. The solvent is removed under reduced pressure, and the residue is purified by chromatography, preferably silica gel, to afford pure racemic amide 8.

EXAMPLE 9

Synthesis of $R_4$ Chroman Esters

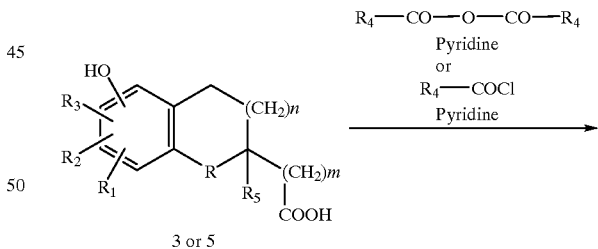

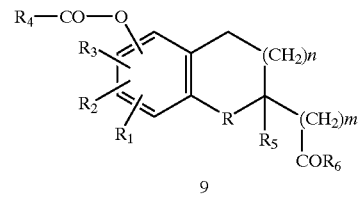

9

Method 1: Chroman 3 ($R_3$=OH) or 5 (10 mmol) is dissolved in pyridine (20 mL), and acid anhydride (30 mmol) is added at 5° C. The reaction mixture is left at room temperature for 18 hours, solvent is removed in vacuum, and the residue is dissolved in ethyl acetate (100 mL), washed with citric acid (10%, 30 mL) and water (30 mL), and dried over sodium sulfate. The solvent is removed and the residue is crystallized from ethyl acetate/hexane to afford ester 9.

Method 2: Chroman 3 ($R_3$=OH) or 5 (10 mmol) is dissolved in dry pyridine (50 mL) under nitrogen and cooled in an ice-water bath. Acyl chloride (10 mmol) is added via syringe over 15 minutes. Stirring is continued for 1 hour at room temperature. Pyridine is removed under reduced pressure, and the residue is dissolved in ethyl acetate (100 mL). The ethyl acetate phase is washed with water (2×40 mL), aqueous hydrochloric acid (0.05 M, 30 mL) and water (40 mL), and dried over sodium sulfate. The solvent is removed under reduced pressure, and the residue is purified by chromatography, preferably on silica gel, to afford ester 9.

EXAMPLE 10

Synthesis of Oxidized Chroman Derivatives

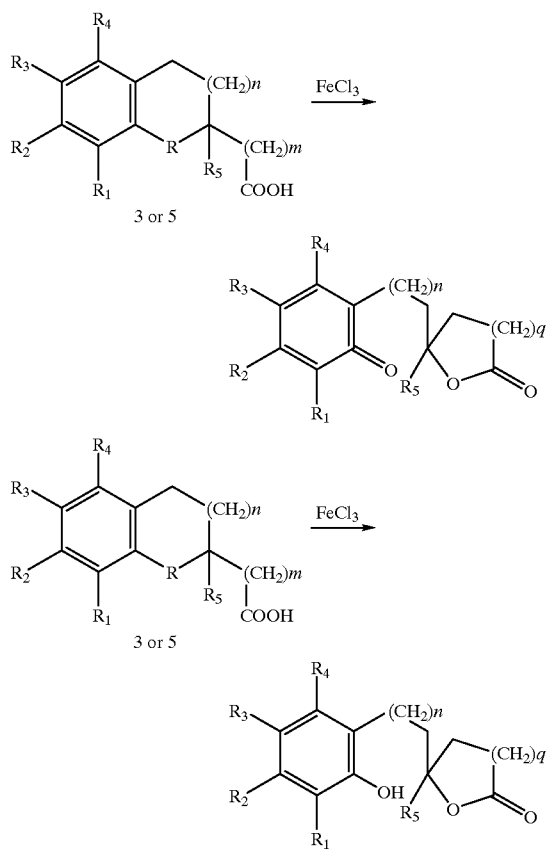

Chroman 3 or 5 (0.3 mmol) is dissolved in methanol (2.5 mL) in a flask. A ferric chloride solution is prepared by dissolving 1.0 g $FeCl_3 \cdot 6H_2O$ in water (4.0 mL) and adding methanol (4.0 mL). The ferric chloride solution (2.5 mL) is added to the flask at room temperature with vigorous stirring for 30 minutes in darkness. Methanol is removed in vacuum, and the residue is dissolved in ether (70 mL). The ether solution is washed with water (3×20 mL) and dried over sodium sulfate, then the solvent is removed. The product is purified on an RP HPLC column ($CH_3CH/H_2O$ gradient) to afford a yellow-to-brown oily product.

EXAMPLE 11

Synthesis of Racemic 2,7,8-Trimethyl-2-(β-carboxyethyl)-6-hydroxy Chroman (LLU-α)

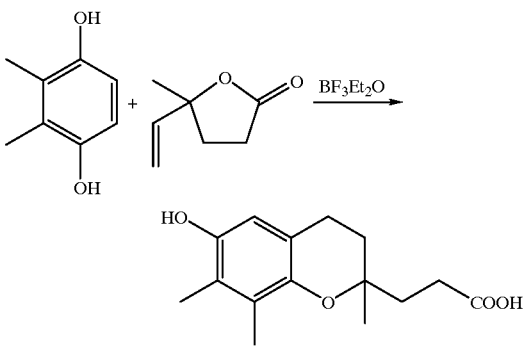

To a solution of 2,3-dimethyl-1,4-hydroquinone (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed under reduced pressure to afford a brown, oily residue. The residue was dissolved in methanol (30 mL), and solvent was removed under reduced pressure. The residue was redissolved in methanol (10 mL), and the flask was purged with nitrogen and stored at 5° C. for 20 hours. The resulting suspension was centrifuged, and the supernatant was removed. The remaining white solid (see Example 21, below) was suspended in aqueous 70% methanol (15 mL) and again centrifuged. The supernatant was combined with the previous supernatant, and methanol was removed in vacuum to afford a brown, oily liquid. The liquid was further purified by flash column chromatography on silica gel (eluant ethyl acetate/hexane/acetic acid, 500:300:1) to afford pure racemic 2,7,8-trimethyl-2-(β-carboxyethyl)-6-hydroxy chroman, which was crystallized from ether-hexane in a yield of 40%. M.P.: 147–148° C.

EXAMPLE 12

Synthesis of Racemic 2,5,7,8-Tetramethyl-2-(β-carboxyethyl)-6-hydroxy Chroman

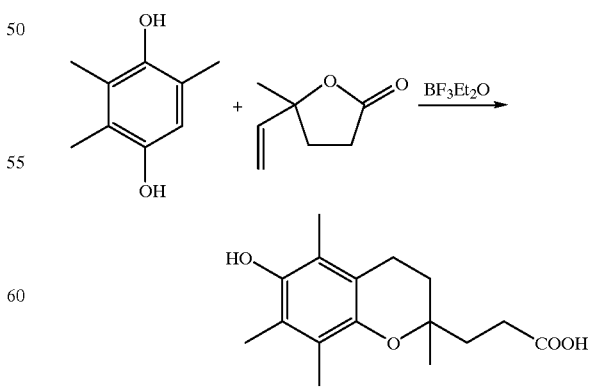

To a solution of 2,3,5-trimethyl-1,4-hydroquinone (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed in vacuum. The residue was dissolved in methanol (30 mL), and solvent was removed in vacuum. The brown, oily residue was dissolved in methanol (20 mL), and water was added until the solution became turbid (app. 20 mL), then the flask was purged with nitrogen and stored overnight in a refrigerator. The light yellow solid was filtered on a sinter funnel, washed with aqueous 50% methanol and dried in a dessicator. The product was further purified by flash column chromatography on silica gel (eluant ethyl acetate/hexane/acetic acid, 500:300:1) to afford pure racemic 2,5,7,8-tetramethyl-2-(β-carboxyethyl)-6-hydroxy chroman, which was crystallized from ether-hexane in a yield of 50%. M.P.: 173° C.

EXAMPLE 13

Synthesis of Racemic 2,5,7,8-Tetramethyl-2-(β-carboxyethyl)-chroman

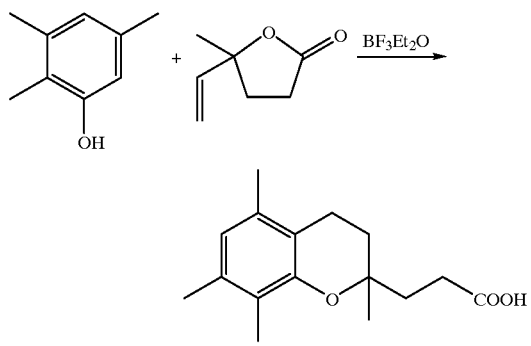

To a solution of 2,3,5-trimethylphenol (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) via syringe pump over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed in vacuum. The residue was dissolved in methanol (30 mL), and solvent was removed in vacuum. The reaction mixture was purified by flash column chromatography on silica gel (eluant ethyl acetate/hexane, 1:1). Fractions containing the desired chroman were pooled, solvent was removed, and the compound was crystallized from ethyl acetate/hexane to afford a white crystalline product in a yield of 40%. M.P.: 148–149° C.

EXAMPLE 14

Synthesis of Racemic 2,7,8-Trimethyl-2-(β-carboxyethyl)chroman

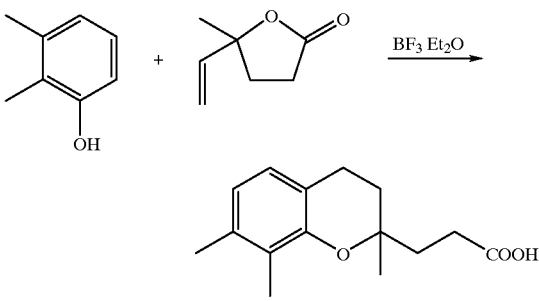

To a solution of 2,3-dimethylphenol (0.01 mol) and boron trifluoride diethyl etherate (0.016 mol) in dioxane (10 mL, dried on sodium) in a flask was added γ-methyl-γ-vinylbutyrolactone (0.016 mol) in dioxane (5.0 mL) via syringe pump over 50 min at 110° C. (oil bath, reflux) under nitrogen. The reaction mixture was cooled to room temperature and diluted with ether (200 mL), then washed with water (100 mL, 2×50 mL) and dried over sodium sulfate. Ether was then removed in vacuum. The residue was dissolved in methanol (30 mL), and solvent was removed in vacuum. The reaction mixture was purified by flash column chromatography on silica gel (eluant ethyl acetate/hexane, 1:1). Fractions containing the desired chroman were pooled, solvent was removed, and the compound was crystallized from ethyl acetate/hexane. M.P.: 93–94° C.

EXAMPLE 15

Synthesis of Racemic 4-Methyl-6-(5,6-dimethylbenzochinoyl)-4-hexanolid

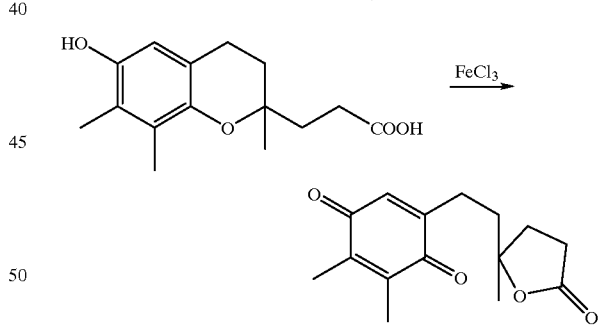

Racemic 2,7,8-trimethyl-2-(β-carboxyethyl)-6-hydroxychroman (100 mg) was dissolved in methanol (2.5 mL) in a flask. A solution of ferric chloride was prepared by dissolving 1.0 g FeCl$_3$.6H$_2$O in water (4.0 mL) and adding methanol (4.0 mL). The ferric chloride solution (2.5 mL) was added to the flask at room temperature with vigorous stirring in darkness for 30 minutes. Methanol was removed in vacuum, and the residue was dissolved in ether (70 mL). The ether solution was washed with water (3×20 mL), dried over sodium sulfate, and the solvent was removed. The product was purified on an RP HPLC column (CH$_3$CN/H$_2$O gradient) to afford a yellow-to-brown oily product in 60% yield.

EXAMPLE 16

Synthesis of Racemic 4-Methyl-6-(3,5,6-trimethylbenzochinoyl)-4-hexanolid

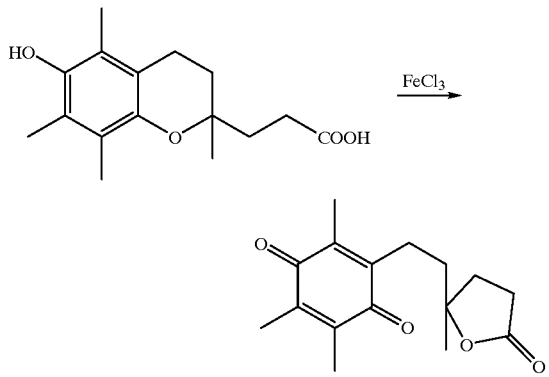

Racemic 2,5,7,8-tetramethyl-2-(β-carboxyethyl)-6-hydroxychroman (100 mg) was dissolved in methanol (2.5 mL) in a flask. The ferric chloride solution of Example 10 (2.5 mL) was added to the flask at room temperature with vigorous stirring in darkness for 30 minutes. Methanol was removed in vacuum, and the residue was dissolved in ether (70 mL). The ether solution was washed with water (3×20 mL), dried over sodium sulfate, and the solvent was removed. The product was purified on an RP HPLC column (CH$_3$CN/H$_2$O gradient) to afford a yellow-to-brown oily product in 60% yield.

EXAMPLE 17

Resolution of Racemic 2,7,8-Trimethyl-2-(β-carboxyethyl)-6-hydroxy chroman (LLU-α)

The resolution of (S) and (R)-enantiomers was carried out on an (S,S)-WHELK-O 1 column (Regis Technologies, Inc.) 250×4.6 mm, 1 mL/min, using as eluant isocratic 80% hexane; 20% propanol:0.5% acetic acid. Fractions were monitored by UV spectroscopy, collected and dried under an argon stream. The enantiomers elute at 6.8 minutes and 8.7 minutes. Isolated LLU-α, when run on this system, elutes at 8.6 minutes.

EXAMPLE 18

Synthesis of (R)- and (S)-4-Methyl-6-(5,6-dimethylbenzochinoyl)-4-hexanolid

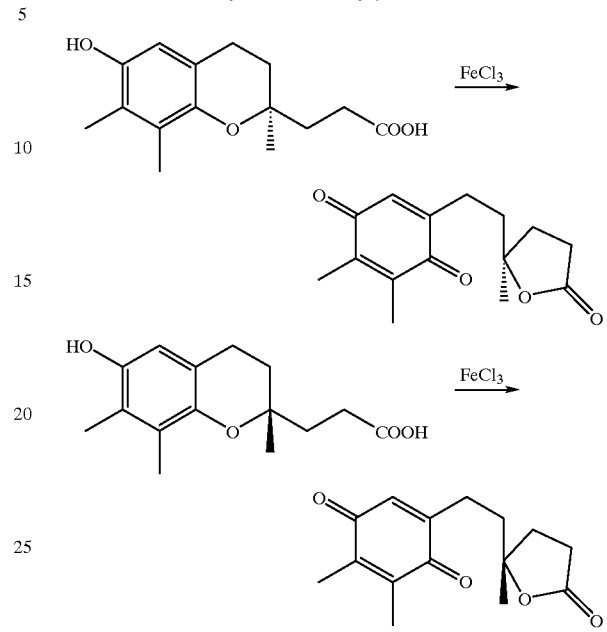

(R)-2,7,8-Trimethyl-2-(β-carboxyethyl)-6-hydroxy chroman (100 mg) (see Example 17) was dissolved in methanol (2.5 mL) and ferric chloride solution (2.5 mL) was added at room temperature with vigorous stirring for 30 minutes in darkness. Methanol was removed under reduced pressure, and the residue was dissolved in ether (70 mL). The ether solution was washed with water (3×20 mL), dried over sodium sulfate, and the solvent was removed. The product was purified by HPLC, using a Phenomenex column (SPHEREX 10 ODS, 250×21.2 mm) with CH$_3$CN—H$_2$O 50:50 for 5 minutes, linear gradient to CH$_3$CN—H$_2$O 90:10 in 30 minutes, linear gradient to 100% CH$_3$CN in 5 minutes, flow rate 6 mL/min. Fractions containing the desired oxidation production were identified by UV spectroscopy. The fractions were pooled, and solvent was removed under reduced pressure to afford (R)-4-Methyl-6-(5,6-dimethylbenzochinoyl)-4-hexanolid as a yellow to brown oil.

The foregoing process was repeated using (S)-2,7,8-Trimethyl-2-(β-carboxyethyl)-6-hydroxy chroman (100 mg) to afford (S)-4-Methyl-6-(5,6-dimethylbenzochinoyl)-4-hexanolid as a yellow to brown oil.

EXAMPLE 19

Synthesis of Racemic 2,7,8-Trimethyl-2-(β-carboxyethyl)-6-acetyl Chroman

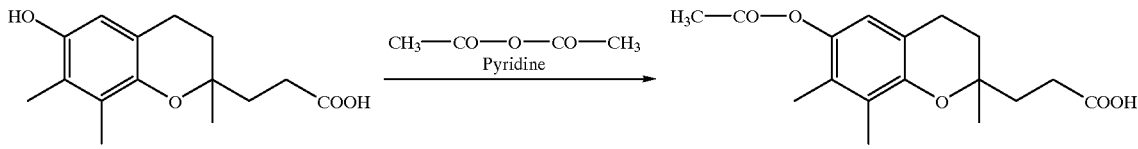

Racemic 2,7,8-Trimethyl-2-(β-carboxyethyl)-6-hydroxy chroman (500 mg) (see Example 11) was dissolved in pyridine (20 mL) at room temperature, and acetic anhydride (10 mL) was added. The solution was maintained at room temperature for 5 hours, solvent was removed under vacuum, methanol (4×10 mL) was added and then removed under reduced pressure. The residual oil was dissolved in ethyl acetate (150 mL) and the organic phase was washed with water (50 mL), aqueous HCl (1 N, 50 mL) and water (50 mL), then dried over sodium sulfate. Solvent was then removed, and the residual oily material was purified on a silica gel column with hexane/ethyl acetate (1:1). The desired product crystallized from acetone/hexane, m.p. 105–107° C.

EXAMPLE 20

Synthesis of Racemic 2,7,8-Trimethyl-2-(β-carboxyethyl)-6-acetyl Chroman Methyl Ester

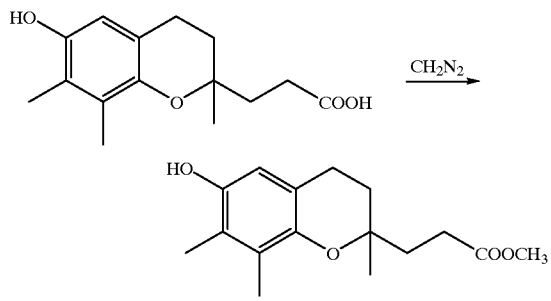

Racemic 2,7,8-Trimethyl-2-(β-carboxyethyl)-6-acetyl chroman (500 mg) (see Examples 11 and 19) was dissolved in methanol (10 mL), and etheral diazomethane was added until the yellow color of diazomethane remained. The solution was maintained at room temperature for 1 hour, solvent was removed, and the residue was purified on a silica gel column with hexane/acetone (3:1). The desired product crystallized from methanol/water, m.p. 87–88° C.

EXAMPLE 21

Synthesis of Benzodipyran Methyl Ester

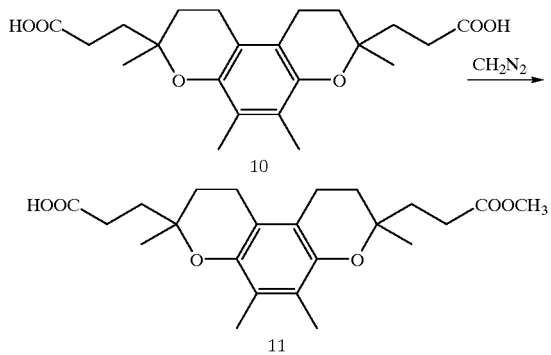

Benzodipyran derivative 10 (m.p. 225–227° C.) was isolated as a reaction byproduct from the synthesis of LLU-α (Example 11). Derivative 10 exists as a racemic mixture of a meso-(R,S) compound and a diastereomeric pair (R,R) and (S,S). Derivative 10 (1.0 g) was suspended in methanol (10 mL), and etheral diazomethane was added until the yellow color of diazomethane remained. The clear solution was maintained at room temperature for 1 hour, solvent was removed, and the residue was purified on a silica gel column with hexane/acetone (3:1). The desired product crystallized from hexane, m.p. 75–76° C.

Although the invention has been described with reference to the presently preferred embodiment, it should be understood that various modifications can be made without departing from the spirit of the invention. Accordingly, the invention is limited only by the following claims.

What is claimed is:

1. A pharmaceutcal composition, comprising a compound having the formula

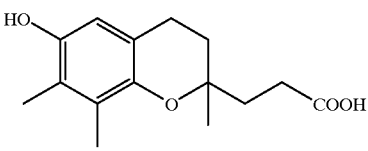

and a pharmaceutically acceptable carrier.

2. A method of stimulating sodium excretion in the urine of a mammal comprising orally or parenterally administering a pharmaceutical composition to said mammal comprising a compound of the formula I

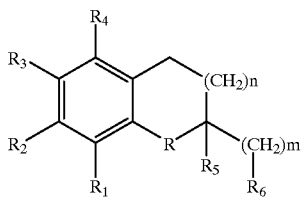

in which

R is O, $R_1$ and $R_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, $R_3$ and $R_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, $R_5$ is H, OH, alkyl, aryl, alkenyl, alkynyl, aromatic, ester or unsubstituted or substituted amine, $R_6$ is COOH, $COOR_7$, $CONH_2$, $CONHR_7$, $CONR_7R_8$, $NH_2$, $NHR_7$, $NR_7R_8$, or a carboxylate salt, $R_7$ and $R_8$ independently are unsubstituted or substituted alkyl, aryl, alkaryl, aralkyl, alkenyl or alkynyl, n is 1, and m is 0 to 5.

3. A method for treating a mammal suffering from hypertension or an edematous condition comprising administering to said mammal a pharmaceutically acceptable carrier and a therapeutically effective amount of a compound of formula I

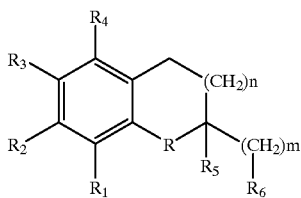

in which

R is O,

R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, R$_3$ and R$_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, R$_5$ is H, OH, alkyl, aryl, alkenyl, alkynyl, aromatic, or ester, R$_6$ is COOH, COOR$_7$, or a carboxylate salt, R$_7$ and R$_8$ independently are unsubstituted or substituted alkyl, aryl, alkaryl, aralkyl, alkenyl or alkynyl, n is 1, and m is 0 to 5.

4. A method for treating a mammal suffering from ischemia comprising administering to said mammal a pharmaceutically acceptable carrier and a therapeutically effective amount of a compound having the formula I

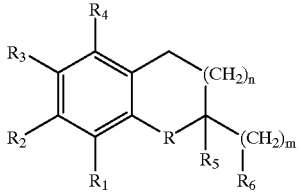

in which

R is O,

R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, R$_3$ and R$_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, provided that R$_4$ is not methyl when R$_3$ is OH, R$_5$ is H, OH, alkyl, aryl, alkenyl, alkynyl, aromatic, ester or unsubstituted or substituted amine, R$_6$ is COOH, COOR$_7$, CONH$_2$, CONHR$_7$, CONR$_7$R$_8$, NH$_2$, NHR$_7$, NR$_7$R$_8$, or a carboxylate salt, R$_7$ and R$_8$ independently are unsubstituted or substituted alkyl, aryl, alkaryl, aralkyl, alkenyl or alkynyl, n is 1, and m is 0 to 5.

5. A method for treating a mammal suffering from angina pectoris comprising administering to said mammal a pharmaceutically acceptable carrier and a therapeutically effective amount of a compound having the formula I

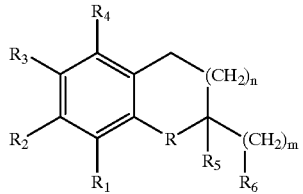

in which

R is O,

R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, R$_3$ and R$_4$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic, aromatic or heterocyclic ring, R$_5$ is H, OH, alkyl, aryl, alkenyl, alkynyl, aromatic, ester or unsubstituted or substituted amine, R$_6$ is COOH, COOR$_7$, CONH$_2$, CONHR$_7$, CONR$_7$R$_8$, NH$_2$, NHR$_7$, NR$_7$R$_8$, or a carboxylate salt, R$_7$ and R$_8$ independently are unsubstituted or substituted alkyl, aryl, alkaryl, aralkyl, alkenyl or alkynyl, n is 1, and m is 0 to 5.

6. A method for treating a mammal suffering from HIV infection or AIDS comprising administering to said mammal a pharmaceutically acceptable carrier and a therapeutically effective amount of a compound having the formula I

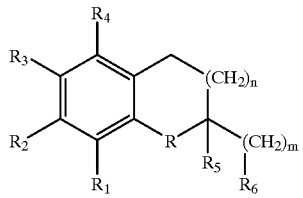

in which

R is O,

R$_1$ and R$_2$ independently are H, OH, alkyl, aryl, alkenyl, alkynyl, aromatic, ether, ester, unsubstituted or substituted amine, amide, halogen or unsubstituted or substituted sulfonyl, or jointly complete a 5- or 6-member aliphatic or aromatic ring, R$_3$ and R$_4$ independently are H, OH, alkyl, aryl, alkenyl, alkynyl, aromatic, ether, ester, unsubstituted or substituted amine, amide, halogen, or unsubstituted or substituted sulfonyl, or jointly complete a 5- or 6-member aliphatic, aromatic or heterocyclic ring, R$_5$ is H, OH, alkyl, aryl, alkenyl, alkynyl, aromatic, ester or unsubstituted or substituted amine, R₆ is COOH, COOR₇, CONH₂, CONHR₇, CONR₇R₈, NH₂, NHR₇, NR₇R₈, or a carboxylate salt, R₇ and R₈ independently are unsubstituted or substituted alkyl, aryl, alkaryl, aralkyl, alkenyl or alkynyl, n is 0 to 3, and m is 0 to 5.

7. The method of claim 2, wherein said compound is

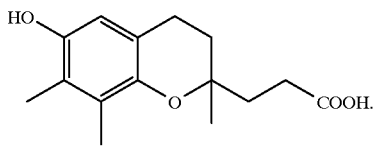

8. The method of claim 3, wherein said compound is

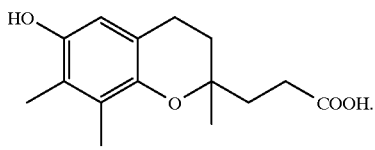

9. The method of claim 4, wherein said compound is

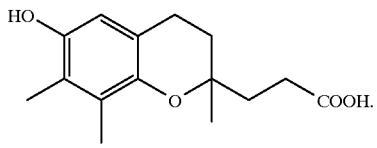

10. The method of claim 5, wherein said compound is

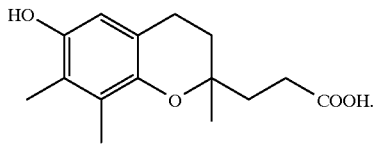

11. The method of claim 6, wherein said compound is

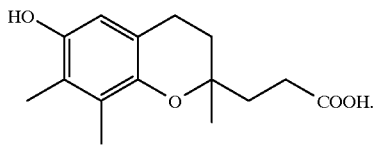

* * * * *